US008088390B2

(12) United States Patent
O'Brien et al.

(10) Patent No.: US 8,088,390 B2
(45) Date of Patent: Jan. 3, 2012

(54) METHODS FOR THE EARLY DIAGNOSIS OF OVARIAN CANCER

(75) Inventors: Timothy J. O'Brien, Little Rock, AR (US); Martin J. Cannon, Little Rock, AR (US); Alessandro Santin, Little Rock, AR (US)

(73) Assignee: Board of Trustees of the University of Arkansas, Little Rock, AK (US)

( * ) Notice: Subject to any disclaimer, the term of this patent is extended or adjusted under 35 U.S.C. 154(b) by 837 days.

(21) Appl. No.: 11/973,468

(22) Filed: Oct. 9, 2007

(65) Prior Publication Data

US 2009/0010842 A1 Jan. 8, 2009

Related U.S. Application Data

(60) Division of application No. 10/372,521, filed on Feb. 21, 2003, now Pat. No. 7,282,198, which is a continuation-in-part of application No. 09/918,243, filed on Jul. 30, 2001, now Pat. No. 6,627,403, which is a continuation-in-part of application No. 09/905,083, filed on Jul. 13, 2001, now Pat. No. 7,306,927, which is a division of application No. 09/502,600, filed on Feb. 11, 2000, now Pat. No. 6,294,344, which is a continuation-in-part of application No. 09/039,211, filed on Mar. 14, 1998, now Pat. No. 6,303,318.

(60) Provisional application No. 60/041,404, filed on Mar. 19, 1997.

(51) Int. Cl.
*A61K 38/08* (2006.01)
*A61K 38/04* (2006.01)
*C07K 5/04* (2006.01)

(52) U.S. Cl. ............... 424/185.1; 530/327; 530/328; 530/350

(58) Field of Classification Search ............ 530/327, 530/328, 350; 424/185, 185.1
See application file for complete search history.

(56) References Cited

FOREIGN PATENT DOCUMENTS
WO WO 9631122 A1 * 10/1996

OTHER PUBLICATIONS

Hansson, L. et al, The Journal of Biological Chemistry, 269(30): 19420-19426, 1994.*
Tanimoto, H. et al. Cancer, 86: 2074-2082, 1999.*
Strynadka, N.C.J., et al., Journal of Virology, 62(9): 3474-3483, 1988.*

* cited by examiner

*Primary Examiner* — Alana Harris Dent
*Assistant Examiner* — Anne Holleran
(74) *Attorney, Agent, or Firm* — Benjamin Aaron Adler

(57) ABSTRACT

The present invention discloses the protease stratum corneum chymotryptic enzyme (SCCE) is specifically over-expressed in ovarian and other malignancies. A number of SCCE peptides can induce immune responses to SCCE, thereby demonstrating the potential of these peptides in monitoring and the development of immunotherapies for ovarian and other malignancies.

1 Claim, 14 Drawing Sheets

1) Normal Ovary  2) Tumor
3) Normal Ovary  4) Tumor

 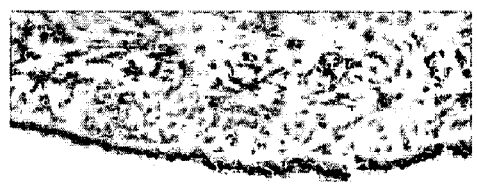
Fig. 10A Fig. 10B
 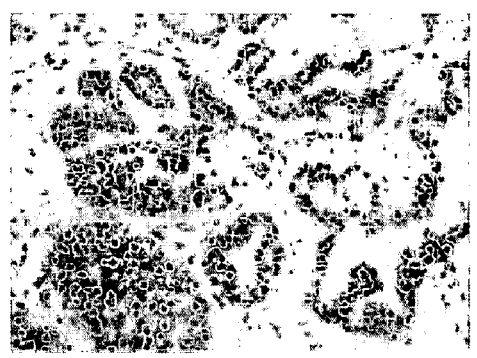
Fig. 10C Fig. 10D
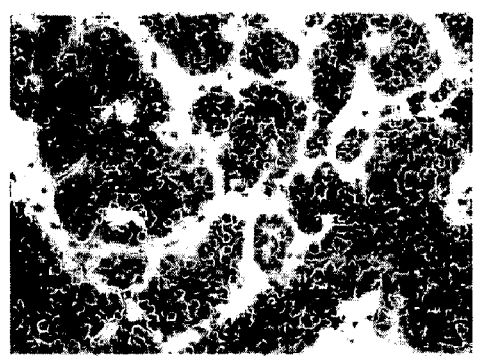 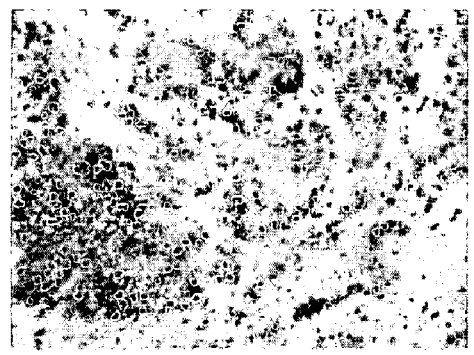
Fig. 10E Fig. 10F

1.                    ↓           15

VVTAAHCVYDLYLPK 16                              30

SWTIQVGLVSLLDNP    ↓   indicates the site of insert in TADG12

31                    45        H & D are the conserved regions of
                                Serine protease.
APSHLVEKIVYHSKY 46           57

KPKRLGNDIALL          SEQ ID NO: 141

1  6    10              53   57
         HCVY DLYL            D        SEQ ID NO: 142
              ↑
         site of 133 bp insert in TADG12

METHODS FOR THE EARLY DIAGNOSIS OF OVARIAN CANCER

CROSS-REFERENCE TO RELATED APPLICATIONS

This is a divisional application of U.S. Ser. No. 10/372,521, filed Feb. 21, 2003, now U.S. Pat. No. 7,282,198 which claims benefit of priority under 35 USC §120 of continuation-in-part application U.S. Ser. No. 09/918,243, filed Jul. 30, 2001, now U.S. Pat. No. 6,627,403, which is a continuation-in-part of U.S. Ser. No. 09/905,083, filed Jul. 13, 2001, U.S. Pat. No. 7,306,927 which is a divisional of U.S. Ser. No. 09/502,600, filed Feb. 11, 2000 now U.S. Pat. No. 6,294,344, now which is a continuation-in-part of U.S. Ser. No. 09/039,211, filed Mar. 14, 1998, now U.S. Pat. No. 6,303,318, which claims benefit of provisional U.S. Ser. No. 60/041,404, filed Mar. 19, 1997, now abandoned.

BACKGROUND OF THE INVENTION

1. Field of the Invention

Generally, the present invention relates to the fields of molecular biology and medicine. More specifically, the present invention is in the field of cancer research, especially ovarian cancer diagnosis.

2. Description of the Related Art

In order for malignant cells to grow, spread or metastasize, they must have the capacity to invade local host tissue, dissociate or shed from the primary tumor, enter and survive in the bloodstream, implant by invasion into the surface of the target organ and establish an environment conducive for new colony growth, including the induction of angiogenic and growth factors. During this progression, natural tissue barriers such as basement membranes and connective tissue have to be degraded. These barriers include collagen, laminin, fibronectin, proteoglycans and extracellular matrix glycoproteins. Degradation of these natural barriers, both those surrounding the primary tumor and at the sites of metastatic invasion, is believed to be brought about by the action of a matrix of extracellular proteases.

Proteases have been classified into four families: serine proteases, metallo-proteases, aspartic proteases and cysteine proteases. Many proteases have been shown to be involved in human disease processes and these enzymes are targets for the development of inhibitors as new therapeutic agents. Certain individual proteases are induced and overexpressed in a diverse group of cancers, and as such, are potential candidates for markers of early diagnosis and targets for possible therapeutic intervention. A group of known protease expressed in various cancers are shown in Table 1.

TABLE 1

| Proteases | Gastric | Brain | Breast | Ovarian |
|---|---|---|---|---|
| Serine | uPA | uPA | NES-1 | NES-1 |
| | PAI-1 | PAI-1 | uPA | uPA |
| | | tPA | | PAI-2 |
| Cysteine: | CatSCCE B | CatSCCE L | CatSCCE B | CatSCCE B |
| | CatSCCE L | | CatSCCE L | CatSCCE L |

TABLE 1-continued

| Proteases | Gastric | Brain | Breast | Ovarian |
|---|---|---|---|---|
| Metallo- | Matrilysin* | Matrilysin | Stromelysin-3 | MMP-2 |
| | Collagenase* | Stromelysin | MMP-8 | |
| | Stromelysin-1* | Gelatinase B | MMP-9 | |
| | | | Gelatinase A | | uPA, Urokinase-type plasminogen activator;
tPA, Tissue-type plasminogen activator;
PAI-I, Plasminogen activator 0 inhibitors;
PAI-2, Plasminogen activator inhibitors;
NES-1, Normal epithelial cell-specific-1;
MMP, Matrix P metallo-protease.
*Overexpressed in gastrointestinal ulcers.

There is a good body of evidence supporting the downregulation or inhibition of individual proteases and the reduction in invasive capacity or malignancy. In work by Clark et al., inhibition of in vitro growth of human small cell lung cancer was demonstrated using a general serine protease inhibitor. More recently, Torres-Rosedo et al. (1993) demonstrated an inhibition of hepatoma tumor cell growth using specific antisense inhibitors for the serine protease hepsin. Metastatic potential of melanoma cells has also been shown to be reduced in a mouse model using a synthetic inhibitor, batimastat, of metallo-proteases. Powell et al. (1993) presented evidence to confirm that the expression of extracellular proteases in a non-metastatic prostate cancer cell line enhances their malignant progression. Specifically, enhanced metastasis was demonstrated after introducing and expressing the PUMP-1 metallo-protease gene. There is also a body of data to support the notion that expression of cell surface proteases on relatively non-metastatic cell types increases the invasive potential of such cells.

To date, ovarian cancer remains the number one killer of women with gynecologic malignant hyperplasia. Approximately 75% of women diagnosed with such cancers are already at an advanced stage (III and IV) of the disease at their initial diagnosis. During the past 20 years, neither diagnosis nor five-year survival rates have greatly improved for these patients. This is substantially due to the high percentage of high-stage initial detection of the disease. Therefore, the challenge remains to develop new markers that improve early diagnosis and thereby reduce the percentage of high-stage initial diagnoses. The ability to disengage from one tissue and re-engage the surface of another tissue is what provides for the morbidity and mortality associated with this disease. Therefore, extracellular proteases may be good candidates for markers of malignant ovarian hyperplasia.

Thus, the prior art is deficient in a tumor marker useful as an indicator of early disease, particularly for ovarian cancers. The present invention fulfills this long-standing need and desire in the art.

SUMMARY OF THE INVENTION

This invention allows for the detection of cancer, especially ovarian cancer, by screening for stratum corneum chymotryptic enzyme (SCCE) mRNA in tissue. Stratum corneum chymotryptic enzyme specifically associates with the surface of 80 percent of ovarian and other tumors. Proteases are considered to be an integral part of tumor growth and metastasis, and therefore, markers indicative of their presence or absence are useful for the diagnosis of cancer. Furthermore, the present invention is useful for treatment, i.e., by inhibiting SCCE or expression of SCCE, for targeted therapy, for vaccination, etc.

The present invention provides methods of vaccinating an individual against SCCE or produce immune-activated cells directed toward SCCE by inoculating an individual with an expression vector encoding a SCCE protein or a fragment thereof.

The present invention also provides methods of immunotherapy targeted toward SCCE in an individual, involving the steps of generating dendritic cells in vitro from peripheral blood drawn from an individual, loading these dendritic cells with SCCE protein or a fragment thereof, then transferring these dendritic cells back to the individual in single or multiple doses. SCCE-loaded or SCCE-expressing dendritic cells can also be used to stimulate SCCE-specific T cell responses in vitro, followed by adoptive immunotherapy in which the individual is given autologous SCCE-specific T cells.

There is also provided a method of monitoring the efficacy of vaccinating an individual with SCCE or SCCE peptide. The method comprises measuring immune responses in response to said SCCE or SCCE peptide, wherein induction of immune responses to said SCCE or SCCE peptide indicates that said individual has been vaccinated against SCCE.

In another embodiment of the present invention, there are provided methods of inhibiting expression of SCCE in a cell by introducing into a cell a vector encoding an antisense SCCE RNA or an antibody that binds the SCCE protein.

In yet another embodiment of the present invention, there is provided a method of targeted therapy to an individual using a compound that has a targeting moiety specific for SCCE and a therapeutic moiety.

In still yet another embodiment of the present invention, there are provided compositions comprising immunogenic fragments of SCCE protein or an oligonucleotide having a sequence complementary to SEQ ID No: 30. Also embodied is a method of treating a neoplastic state in an individual with an effective dose of the above-described oligonucleotide.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIG. 10A shows normal surface ovarian epithelium. Little SCCE expression was observed (normal ovary, X100). FIG. 10B is a negative control section for FIG. 10A. No nonspecific staining was observed (Normal ovary, X100). FIG. 10C shows positive SCCE staining localized in the cytoplasm and the cell membrane of ovarian cancer cells (case 947, clear cell adenocarcinoma, X100). FIG. 10D is a negative control section for FIG. 10C. No nonspecific staining was observed (case 947, clear cell adenocarcinoma, X100). FIG. 10E is positive stratum corneum chymotryptic enzyme staining localized in the cytoplasm and the cell membrane of ovarian cancer cells. Mucin in the glands also showed positive stratum corneum chymotryptic enzyme staining (case 947, clear cell adenocarcinoma, X100). FIG. 10F is a negative control section for FIG. 10E. No nonspecific staining was observed (case 947, clear cell adenocarcinoma, X100).

DETAILED DESCRIPTION OF THE INVENTION

Figure 1:
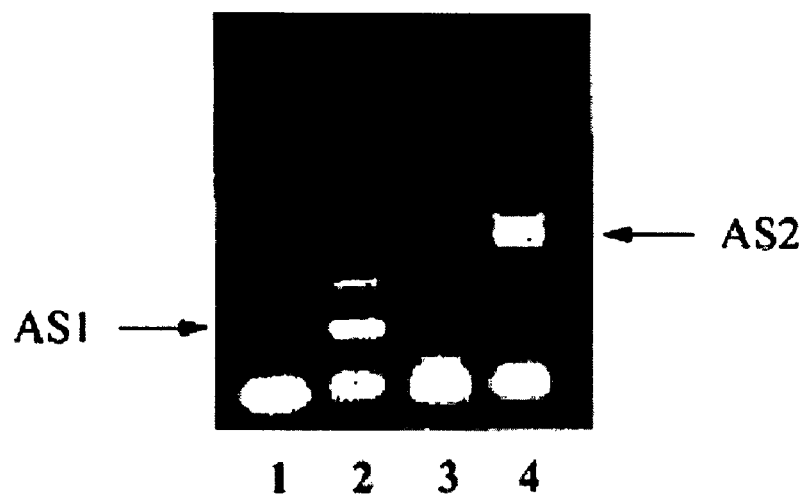
FIG. 1 shows agarose gel comparison of PCR products derived from normal and carcinoma cDNA.

This invention identifies stratum corneum chymotryptic enzyme (SCCE) as a marker for ovarian tumor cells. In various combinations with other proteases, stratum corneum chymotryptic enzyme expression is characteristic of individual tumor types. Such information can provide the basis for diagnostic tests (assays or immunohistochemistry) and prognostic evaluation (depending on the display pattern).

Long-term treatment of tumor growth, invasion and metastasis has not succeeded with existing chemotherapeutic agents. Most tumors become resistant to drugs after multiple cycles of chemotherapy. The present invention identifies SCCE as a new therapeutic intervention target utilizing either antibodies directed at the protease, antisense vehicles for downregulation or protease inhibitors both from established inhibition data and/or for the design of new drugs.

The present invention provides a method of vaccinating an individual against SCCE, comprising the steps of inoculating an individual with an expression vector encoding a SCCE peptide or with peptide-loaded dendritic cells. Expression of the SCCE peptide elicits an immune response in the individual, thereby vaccinating the individual against SCCE. Generally, this method is applicable when the individual has cancer or is at risk of getting a cancer such as ovarian cancer, lung cancer, prostate cancer, pancreatic cancer and colon cancer. Sequences of preferred SCCE peptides are shown in SEQ ID NOS: 31, 32, 33, 34, 35, 36, 80, 86 and 99.

The present invention also provides a method of producing immune-activated cells directed toward SCCE, comprising the steps of exposing immune cells to SCCE protein or fragment thereof. Typically, exposure to SCCE protein or fragment thereof activates the immune cells, thereby producing immune-activated cells directed toward SCCE. Generally, the immune-activated cells are B-cells, T-cells and/or dendritic cells. Preferably, the SCCE fragment is a 9-residue fragment up to a 20-residue fragment, and more preferably, the fragment is SEQ ID NOS: 31, 32, 33, 34, 35, 36, 80, 86 and 99. Oftentimes, the dendritic cells are isolated from an individual prior to exposure and then reintroduced into the individual subsequent to the exposure. Typically, the individual has cancer or is at risk of getting a cancer such as ovarian cancer, lung cancer, prostate cancer and colon cancer.

The present invention also provides methods of immunotherapy targeted toward SCCE in an individual. In one embodiment, the method involves generating dendritic cells in vitro from peripheral blood drawn from the individual, loading these dendritic cells with SCCE protein or a fragment thereof by lipofection or other means, then transferring these dendritic cells back to the individual in single or multiple doses. SCCE may also be expressed in these dendritic cells following transduction with a recombinant DNA vector. Alternatively, SCCE-loaded or SCCE-expressing dendritic cells can be used to stimulate SCCE-specific T cell responses in vitro, followed by adoptive immunotherapy in which the individual is given autologous SCCE-specific T cells. Typically, the individual has cancer or is at risk of getting a cancer such as ovarian cancer, lung cancer, prostate cancer, pancreatic cancer and colon cancer. In general, a full length or a fragment of SCCE protein is expressed in the isolated dendritic cells. Preferably, the fragment is a 9-residue fragment up to a 20-residue fragment, and more preferably, the fragment is SEQ ID NOS: 31, 32, 33, 34, 35, 36, 80, 86 and 99.

There is also provided a method of monitoring the efficacy of vaccinating an individual with SCCE or SCCE peptide such as those shown in SEQ ID NOS: 31, 32, 33, 34, 35, 36, 80, 86 and 99. The method comprises isolating T cells or CD8+ T cells from the vaccinated individual and measuring immune responses specific to the SCCE or SCCE peptide. An increased level of immune responses compared to those exhibited by cells from normal individual indicates that said individual has been vaccinated by the SCCE or SCCE peptide. In general, the individual is vaccinated to SCCE if there is an increased level of SCCE-specific T cells proliferation, an increased frequency of SCCE-specific T cells or an increased frequency of SCCE-specific cytokine-secreting T cells. Standard assays well-known in the art such as tetramer analysis and ELISPOT assay can be used to determine the frequency of SCCE-specific T cells and the frequency of SCCE-specific cytokine-secreting T cells respectively.

In another aspect of the present invention, there is provided a method of inhibiting expression of SCCE in a cell, comprising the step of introducing into a cell a vector comprises a sequence complementary to SEQ ID NO: 30, wherein expression of the vector produces SCCE antisense RNA in the cell.

The SCCE antisense RNA hybridizes to endogenous SCCE mRNA, thereby inhibiting expression of SCCE in the cell.

Expression of SCCE can also be inhibited by antibody. An antibody specific for a SCCE protein or a fragment thereof is introduced into a cell, and binding of the antibody to SCCE would inhibit the SCCE protein. Preferably, the SCCE fragment is a 9-residue fragment up to a 20-residue fragment, and more preferably, the fragment is SEQ ID NOS: 31, 32, 33, 34, 35, 36, 80, 86 and 99.

The present invention is also directed toward a method of targeted therapy to an individual, comprising the step of administering a compound to an individual, wherein the compound has a targeting moiety specific for SCCE and a therapeutic moiety. Preferably, the targeting moiety is an antibody specific for SCCE, a ligand or ligand binding domain that binds SCCE. Likewise, the therapeutic moiety is preferably a radioisotope, a toxin, a chemotherapeutic agent, an immune stimulant or cytotoxic agent. Generally, the individual suffers from a disease such as ovarian cancer, lung cancer, prostate cancer, colon cancer, pancreatic cancer or another cancer in which SCCE is overexpressed.

The present invention is further directed toward an immunogenic composition, comprising an appropriate adjuvant and an immunogenic full length SCCE protein or a fragment thereof. Preferably, the fragment is a 9-residue fragment up to a 20-residue fragment, and more preferably, the fragment is SEQ ID NOS: 31, 32, 33, 34, 35, 36, 80, 86 and 99.

The present invention also provides an oligonucleotide having a sequence complementary to SEQ ID NO: 30 or a fragment thereof. The present invention further provides a composition comprising the above-described oligonucleotide and a physiologically acceptable carrier, and a method of treating a neoplastic state in an individual, comprising the step of administering to the individual an effective dose of the above-described oligonucleotide. Typically, the neoplastic state may be ovarian cancer, breast cancer, lung cancer, colon cancer, prostate cancer, pancreatic cancer or another cancer in which SCCE is overexpressed.

It will be apparent to one skilled in the art that various substitutions and modifications may be made to the invention disclosed herein without departing from the scope and spirit of the invention.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual" (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. 1985); "Transcription and Translation" (B. D. Hames & S. J. Higgins eds. 1984); "Animal Cell Culture" (R. I. Freshney, ed. 1986); "Immobilized Cells And Enzymes" (IRL Press, 1986); B. Perbal, "A Practical Guide To Molecular Cloning" (1984). Therefore, if appearing herein, the following terms shall have the definitions set out below.

As used herein, the term "cDNA" shall refer to the DNA copy of the mRNA transcript of a gene.

As used herein, the term "PCR" refers to the polymerase chain reaction that is the subject of U.S. Pat. Nos. 4,683,195 and 4,683,202 to Mullis, as well as other improvements now known in the art.

The present invention comprises a vector comprising a DNA sequence which encodes a SCCE protein, wherein said vector is capable of replication in a host, and comprises, in operable linkage: a) an origin of replication; b) a promoter; and c) a DNA sequence coding for said SCCE protein. Preferably, the vector of the present invention contains a portion of the DNA sequence shown in SEQ ID NO: 30. Vectors may be used to amplify and/or express nucleic acid encoding a SCCE protein, a fragment of SCCE protein, or an antisense SCCE mRNA.

An expression vector is a replicable construct in which a nucleic acid sequence encoding a polypeptide is operably linked to suitable control sequences capable of effecting expression of the polypeptide in a cell. The need for such control sequences will vary depending upon the cell selected and the transformation method chosen. Generally, control sequences include a transcriptional promoter and/or enhancer, suitable mRNA ribosomal binding sites and sequences which control the termination of transcription and translation. Methods which are well known to those skilled in the art can be used to construct expression vectors containing appropriate transcriptional and translational control signals. See, for example, techniques described in Sambrook et al., 1989, *Molecular Cloning: A Laboratory Manual* (2nd Ed.), Cold Spring Harbor Press, N.Y. A gene and its transcription control sequences are defined as being "operably linked" if the transcription control sequences effectively control transcription of the gene. Vectors of the invention include, but are not limited to, plasmid vectors and viral vectors. Preferred viral vectors of the invention are those derived from retroviruses, adenovirus, adeno-associated virus, SV40 virus, or herpes viruses.

As used herein, the term "host" is meant to include not only prokaryotes but also eukaryotes such as yeast, plant and animal cells. A recombinant DNA molecule or gene which encodes a human SCCE protein of the present invention can be used to transform a host using any of the techniques commonly known to those of ordinary skill in the art. Especially preferred is the use of a vector containing coding sequences for the gene which encodes a human SCCE protein of the present invention for purposes of prokaryote transformation. Prokaryotic hosts may include *E. coli, S. tymphimurium, Serratia marcescens* and *Bacillus subtilis*. Eukaryotic hosts include yeasts such as *Pichia pastoris*, mammalian cells and insect cells.

The term "oligonucleotide", as used herein, is defined as a molecule comprised of two or more ribonucleotides, preferably more than three. Its exact size will depend upon many factors, which, in turn, depend upon the ultimate function and use of the oligonucleotide. The term "primer", as used herein, refers to an oligonucleotide, whether occurring naturally (as in a purified restriction digest) or produced synthetically, and which is capable of initiating synthesis of a strand complementary to a nucleic acid when placed under appropriate conditions, i.e., in the presence of nucleotides and an inducing agent, such as a DNA polymerase, and at a suitable temperature and pH. The primer may be either single-stranded or double-stranded and must be sufficiently long to prime the synthesis of the desired extension product in the presence of the inducing agent. The exact length of the primer will depend upon many factors, including temperature, sequence and/or homology of primer and the method used. For example, in diagnostic applications, the oligonucleotide primer typically contains 15-25 or more nucleotides, depending upon the complexity of the target sequence, although it may contain fewer nucleotides.

The primers herein are selected to be "substantially" complementary to particular target DNA sequences. This means that the primers must be sufficiently complementary to hybridize with their respective strands. Therefore, the primer sequence need not reflect the exact sequence of the template.

For example, a non-complementary nucleotide fragment, i.e., containing a restriction site, may be attached to the 5' end of the primer, with the remainder of the primer sequence being complementary to the strand. Alternatively, non-complementary bases or longer sequences can be interspersed into the primer, provided that the primer sequence has sufficient complementary with the sequence to hybridize therewith and form the template for synthesis of the extension product.

As used herein, "substantially pure DNA" means DNA that is not part of a milieu in which the DNA naturally occurs, by virtue of separation (partial or total purification) of some or all of the molecules of that milieu, or by virtue of alteration of sequences that flank the claimed DNA. The term therefore includes, for example, a recombinant DNA which is incorporated into a vector, into an autonomously replicating plasmid or virus, or into the genomic DNA of a prokaryote or eukaryote; or which exists as a separate molecule, e.g., a cDNA or a genomic or cDNA fragment produced by polymerase chain reaction (PCR) or restriction endonuclease digestion, independent of other sequences. It also includes a recombinant DNA which is part of a hybrid gene encoding additional polypeptide sequence, e.g., a fusion protein. Also included is a recombinant DNA which includes a portion of the nucleotides listed in SEQ ID NO: 30 and which encodes an alternative splice variant of SCCE.

The DNA may have at least about 70% sequence identity to the coding sequence of the nucleotides listed in SEQ ID NO: 30, preferably at least 75%, e.g., at least 80%; and most preferably at least 90%. The identity between two sequences is a direct function of the number of matching or identical positions. When a position in both of the two sequences is occupied by the same monomeric subunit, e.g., if a given position is occupied by an adenine in each of two DNA molecules, then they are identical at that position. For example, if 7 positions in a sequence 10 nucleotides in length are identical to the corresponding positions in a second 10-nucleotide sequence, then the two sequences have 70% sequence identity. The length of comparison sequences will generally be at least 50 nucleotides, preferably at least 60 nucleotides, more preferably at least 75 nucleotides, and most preferably 100 nucleotides. Sequence identity is typically measured using sequence analysis software (Sequence Analysis Software Package of the Genetics Computer Group (GCG), University of Wisconsin Biotechnology Center, 1710 University Avenue, Madison, Wis. 53705).

Further included in this invention are SCCE proteins which are encoded, at least in part, by portions of SEQ ID NO: 30, e.g., products of alternative mRNA splicing or alternative protein processing events, or in which a section of SCCE sequence has been deleted. The fragment, or the intact SCCE polypeptide, may be covalently linked to another polypeptide, e.g., one which acts as a label, a ligand or a means to increase antigenicity.

A substantially pure SCCE protein may be obtained, for example, by extraction from a natural source; by expression of a recombinant nucleic acid encoding a SCCE polypeptide; or by chemically synthesizing the protein. Purity can be measured by any appropriate method, e.g., column chromatography, such as immunoaffinity chromatography using an antibody specific for SCCE, polyacrylamide gel electrophoresis, or HPLC analysis. A protein is substantially free of naturally associated components when it is separated from at least some of those contaminants which accompany it in its natural state. Thus, a protein which is chemically synthesized or produced in a cellular system different from the cell from which it naturally originates will be, by definition, substantially free from its naturally associated components. Accordingly, substantially pure proteins include eukaryotic proteins synthesized in $E.\ coli$, other prokaryotes, or any other organism in which they do not naturally occur.

In addition to substantially full-length proteins, the invention also includes fragments, e.g., antigenic fragments, of the SCCE protein. As used herein, "fragment," as applied to a polypeptide, will ordinarily be at least 10 residues, more typically at least 20 residues, and preferably at least 30, e.g., 50, residues in length, but less than the entire, intact sequence. Fragments of the SCCE protein can be generated by methods known to those skilled in the art, e.g., by enzymatic digestion of naturally occurring or recombinant SCCE protein, by recombinant DNA techniques using an expression vector that encodes a defined fragment of SCCE, or by chemical synthesis. The ability of a candidate fragment to exhibit a characteristic of SCCE, e.g., binding to an antibody specific for SCCE, can be assessed by methods known in the art.

Purified SCCE or antigenic fragments of SCCE can be used to generate new antibodies or to test existing antibodies, e.g., as positive controls in a diagnostic assay) by employing standard protocols known to those skilled in the art. Included in this invention is polyclonal antisera generated by using SCCE or a fragment of SCCE as the immunogen in, e.g., rabbits. Standard protocols for monoclonal and polyclonal antibody production known to those skilled in this art are employed. The monoclonal antibodies generated by this procedure can be screened for the ability to identify recombinant SCCE cDNA clones, and to distinguish them from other cDNA clones.

The invention encompasses not only an intact anti-SCCE monoclonal antibody, but also an immunologically-active antibody fragment, e.g., a Fab or $(Fab)_2$ fragment; an engineered single chain Fv molecule; or a chimeric molecule, e.g., an antibody which contains the binding specificity of one antibody, e.g., of murine origin, and the remaining portions of another antibody, e.g., of human origin.

In one embodiment, the antibody, or a fragment thereof, may be linked to a toxin or to a detectable label, e.g., a radioactive label, non-radioactive isotopic label, fluorescent label, chemiluminescent label, paramagnetic label, enzyme label, or colorimetric label well-known in the art. Examples of suitable toxins include diphtheria toxin, $Pseudomonas$ exotoxin A, ricin, and cholera toxin. Examples of suitable enzyme labels include alkaline phosphatase, beta-galactosidase, ribonuclease, urease, catalase, glucose-6-phosphate dehydrogenase, etc. Examples of suitable radioisotopic labels include $^3H$, $^{125}I$, $^{131}I$, $^{32}P$, $^{35}S$, $^{14}C$, etc.

Paramagnetic isotopes for purposes of in vivo diagnosis can also be used according to the methods of this invention. There are numerous examples of elements that are useful in magnetic resonance imaging. For discussions on in vivo nuclear magnetic resonance imaging, see, for example, Schaefer et al., (1989) $JACC$ 14:472-480; Shreve et al., (1986) $Magn.\ Reson.\ Med.$ 3:336-340; Wolf, G. L., (1984) $Physiol.\ Chem.\ Phys.\ Med.\ NMR$ 16:93-95; Wesbey et al., (1984) $Physiol.\ Chem.\ Phys.\ Med.\ NMR$ 16:145-155; Runge et al., (1984) $Invest.\ Radiol.$ 19:408-415. Examples of suitable fluorescent labels include a fluorescein label, an isothiocyalate label, a rhodamine label, a phycoerythrin label, a phycocyanin label, an allophycocyanin label, an ophthaldehyde label, a fluorescamine label, etc. Examples of chemiluminescent labels include a luminal label, an isoluminal label, an aromatic acridinium ester label, an imidazole label, an acridinium salt label, an oxalate ester label, a luciferin label, a luciferase label, an aequorin label, etc.

Those of ordinary skill in the art will know of other suitable labels which may be employed in accordance with the present invention. The binding of these labels to antibodies or fragments thereof can be accomplished using standard techniques commonly known and used by those of ordinary skill in the art. Typical techniques are described by Kennedy et al., (1976) *Clin. Chim. Acta* 70, 1-31; and Schurs et al., (1977) *Clin. Chim. Acta* 81, 1-40. Coupling techniques mentioned in the latter are the glutaraldehyde method, the periodate method, the dimaleimide method, the m-maleimidobenzyl-N-hydroxy-succinimide ester method. All of these methods are incorporated by reference herein.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Amplification of Serine Proteases Using Redundant and Specific Primers

Only cDNA preparations deemed free of genomic DNA were used for gene expression analysis. Redundant primers were prepared for serine proteases, metallo-proteases and cysteine protease. The primers were synthesized to consensus sequences of amino acid surrounding the catalytic triad for serine proteases, viz. histidine . . . aspartate . . . and serine. The sequences of both sense (histidine & aspartate) and antisense (aspartate and serine) redundant primers are shown in Table 2.

TABLE 2

| PCR Primers | 5'→3' | SEQ ID NO: |
|---|---|---|
| Redundant Primers: | | |
| Serine Protease (histidine) = S1 | tgggtigtiacigcigcica(ct)tg | 1 |
| Serine Protease (aspartic acid) = AS1 | a(ag)ia(ag)igciatitcitticc | 2 |
| Serine Protease (serine) = AS11 | a(ag)iggiccicci(cg)(ta)(ag)tcicc | 3 |
| Cysteine Protease - sense | ca(ag)ggica(ag)tg(ct)ggi(ta)(cg)itg(ct)tgg | 4 |
| Cysteine Protease - antisense | taiccicc(ag)tt(ag)caicc(ct)tc | 5 |
| Metallo Protease - sense | cci(ac)gitg(tc)ggi(ga)(ta)icciga | 6 |
| Metallo Protease - antisense | tt(ag)tgicciai(ct)tc(ag)tg | 7 |
| Specific Primers: | | |
| Serine Protease (SCCE) = sense | tgtcccgatggcgagtgttt | 8 |
| Serine Protease (SCCE) = antisense | cctgttggccatagtactgc | 9 |
| Serine Protease (SCCE) = sense | agatgaatgagtacaccgtg | 10 |
| Serine Protease (SCCE) = antisense | ccagtaagtccttgtaaacc | 11 |
| Serine Protease (Comp B) = sense | aagggacacgagagctgtat | 12 |
| Serine Protease (Comp B) = antisense | aagtggtagttggaggaagc | 13 |
| Serine Protease (Protease M) = sense | ctgtgatccaccctgactat | 20 |
| Serine Protease (Protease M) = antisense | caggtggatgtatgcacact | 21 |
| Serine Protease (TADG12) = sense (Ser10-s) | gcgcactgtgtttatgagat | 22 |
| Serine Protease (TADG12) = antisense (Ser10-as) | ctctttggcttgtacttgct | 23 |
| Serine Protease (TADG13) = sense | tgagggacatcattatgcac | 24 |
| Serine Protease (TADG13) = antisense | caagttttccccataattgg | 25 |
| Serine Protease (TADG14) = sense | acagtacgcctgggagacca | 26 |
| Serine Protease (TADG14) = antisense | ctgagacggtgcaattctgg | 27 |
| Cysteine Protease (Cath-L) = sense | attggagagagaaaggctac | 14 |
| Cysteine Protease (Cath-L) = antisense | cttgggattgtacttacagg | 15 |
| Metallo Protease (PUMP1) = sense | cttccaaagtggtcacctac | 16 |
| Metallo Protease (PUMP1) = antisense | ctagactgctaccatccgtc | 17 |

EXAMPLE 2

Carcinoma Tissue

Several protease entities were identified and subcloned from PCR amplification of cDNA derived from serous cystadenocarcinomas. Therefore, the proteases described herein are reflective of surface activities for this type of carcinoma, the most common form of ovarian cancer. It was also shown that PCR amplification bands unique to the mucinous tumor type and the clear cell type have similar base pair size. About 20-25% of ovarian cancers are classified as either mucinous, clear cell, or endometrioid.

EXAMPLE 3

Ligation, Transformation and Sequencing

To determine the identity of the PCR products, all the appropriate bands were ligated into Promega T-vector plasmid and the ligation product was used to transform JM109 cells (Promega) grown on selective media. After selection and culturing of individual colonies, plasmid DNA was isolated by means of the WIZARD MINIPREP™ DNA purification system (Promega). Inserts were sequenced using a Prism Ready Reaction Dydeoxy Terminators cycle sequencing kit (Applied Biosystems). Residual dye terminators were removed from the completed sequencing reaction using a CENTRISEP SPIN™ column (Princeton Separation), and samples were loaded into an Applied Biosystems Model 373A DNA sequencing system. The results of subcloning and sequencing for the serine protease primers are summarized in Table 3.

TABLE 3

| Subclone | Primer Set | Gene Candidate |
|---|---|---|
| 1 | His-Ser | SCCE |
| 2 | His-Ser | SCCE |
| 3 | His-Ser | Compliment B |
| 4 | His-Asp | Cofactor 1 |
| 5 | His-Asp | TADG-12* |
| 6 | His-Ser | TADG-13* |
| 7 | His-Ser | TADG-14* |
| 8 | His-Ser | Protease M |
| 9 | His-Ser | TADG-15* |

*indicates novel proteases

EXAMPLE 4

Cloning and Characterization

Cloning and characterization of new gene candidates was undertaken to expand the panel representative of extracellular proteases specific for ovarian carcinoma subtypes. Sequencing of the PCR products derived from tumor cDNA confirms the potential candidacy of these genes. The three novel genes all have conserved residues within the catalytic triad sequence consistent with their membership in the serine protease family.

PCR products amplified from normal and carcinoma cDNAs were compared using sense-histidine and antisense-aspartate as well as sense-histidine and antisense-serine. The anticipated PCR products of approximately 200 bp and 500 bp for those pairs of primers were observed. Aspartate is approximately 50-70 amino acids downstream from histidine and serine is about 100-150 amino acids toward the carboxy end from histidine.

FIG. 1 shows a comparison of PCR products derived from normal and carcinoma cDNA as shown by staining in an agarose gel. Two distinct bands in Lane 2 were present in the primer pair sense-His/antisense ASP (AS1) and multiple bands of about 500 bp are noted in the carcinoma lane for the sense-His/antisense-Ser (AS2) primer pairs in Lane 4.

EXAMPLE 5

Quantitative PCR

The mRNA overexpression of SCCE was detected and determined using quantitative PCR. Quantitative PCR was performed generally according to the method of Noonan et al. (1990). The following oligonucleotide primers were used: SCCE: forward 5'-AGATGAATGAGTACACCGTG-3' (SEQ ID NO: 10), and reverse 5'-CCAGTAAGTCCTTGTAAACC-3' (SEQ ID NO: 11); and β-tubulin: forward 5'-TGCATTGA-CAACGAGGC-3' (SEQ ID NO: 18), and reverse 5'-CT-GTCTTGA CATTGTTG-3' (SEQ ID NO: 19). β-tubulin was utilized as an internal control.

The predicted sizes of the amplified genes were 339 bp for SCCE and 454 bp for β-tubulin. The primer sequences used in this study were designed according to the cDNA sequences described by Hansson et al. (1994) for SCCE, and Hall et al. (1983) for β-tubulin. The PCR reaction mixture consisted of cDNA derived from 50 ng of mRNA converted by conventional techniques, 5 μmol of sense and antisense primers for both the SCCE gene and the β-tubulin gene, 200 μmol of dNTPs, 5 μCi of $\alpha$-$^{32}$PdCTP and 0.25 units of Taq DNA polymerase with reaction buffer (Promega) in a final volume of 25 μl. The target sequences were amplified in parallel with the β-tubulin gene. Thirty cycles of PCR were carried out in a Thermal Cycler (Perkin-Elmer Cetus). Each cycle of PCR included 30 sec of denaturation at 95° C., 30 sec of annealing at 63° C. and 30 sec of extension at 72° C. It was previously established and confirmed for SCCE that co-amplification with β-tubulin under these conditions for 30 cycles remain linear for both products.

The PCR products were separated on 2% agarose gels and the radioactivity of each PCR product was determined by using a Phospho Imager (Molecular Dynamics). In the present study, expression of SCCE was calculated as the ratio (SCCE/β-tubulin) as measured by phosphoimager. The overexpression cut-off value was defined as the mean value for normal ovary +2SD. The student's t test was used for the comparison of the mean values of normal ovary and tumors.

Figure 2:
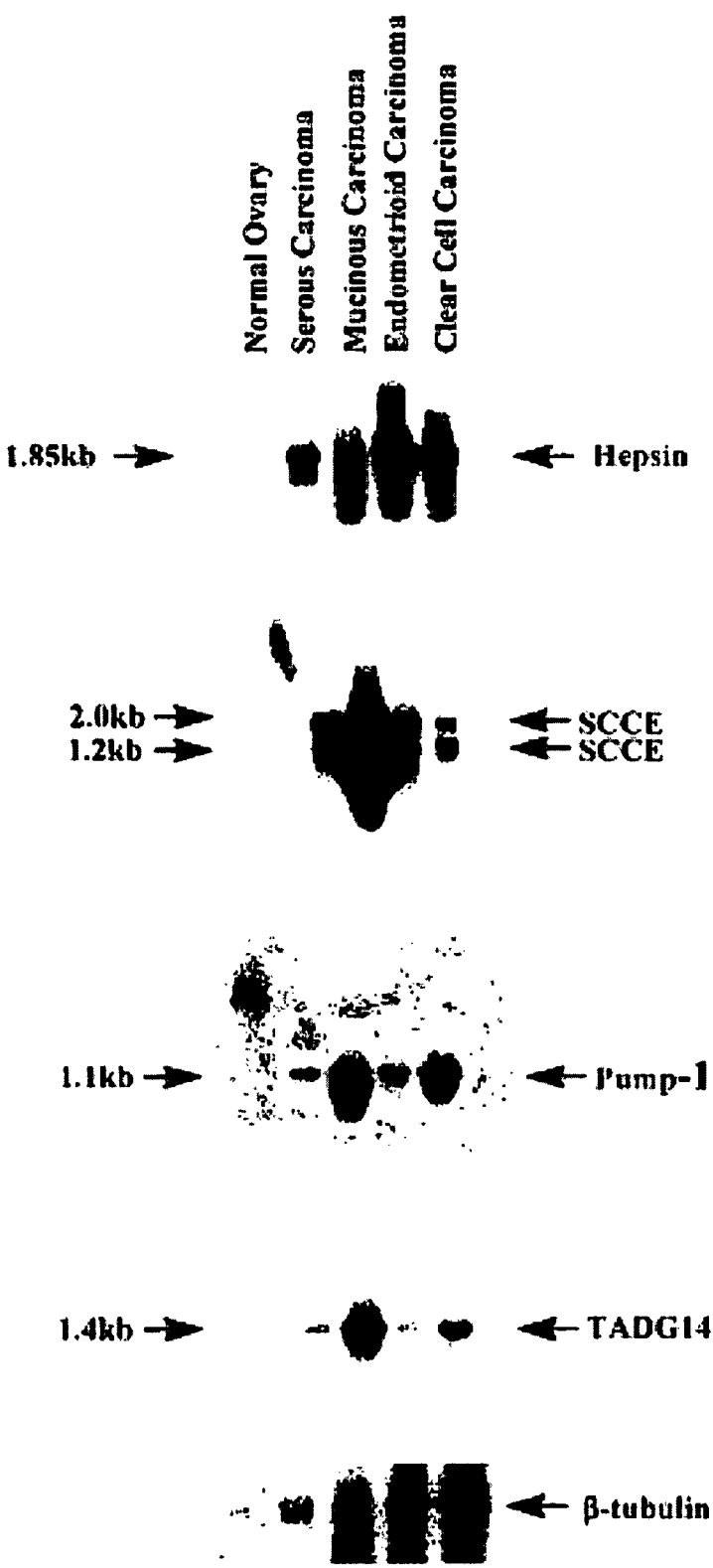
FIG. 2 shows Northern blot analysis of ovarian tumors using SCCE, SCCE, PUMP-1, TADG-14 and β-tubulin probes.

Experiments comparing PCR amplification in normal ovary and ovarian carcinoma suggested overexpression and/or alteration in mRNA transcript in tumor tissues. Northern blot analysis of TADG-14 confirms a transcript size of 1.4 kb and data indicate overexpression in ovarian carcinoma (FIG. 2). Isolation and purification using both PCR and a specific 250 bp PCR product to screen positive plaques yielded a 1.2 kb clone of TADG-14. Other proteases were amplified by the same method using the appropriate primers from Table 2.

EXAMPLE 6

Tissue Bank

A tumor tissue bank of fresh frozen tissue of ovarian carcinomas as shown in Table 4 was used for evaluation.

Approximately 100 normal ovaries removed for medical reasons other than malignancy were obtained from surgery and were available as controls.

TABLE 4

|  | Total | Stage I/11 | Stage III/IV | No Stage |
|---|---|---|---|---|
| Serous |  |  |  |  |
| Malignant | 166 | 15 | 140 | 8 |
| LMP | 16 | 9 | 7 | 0 |
| Benign | 12 | 0 | 0 | 12 |
| Mucinous |  |  |  |  |
| Malignant | 26 | 6 | 14 | 6 |
| LMP | 28 | 25 | 3 | 0 |
| Benign | 3 | 0 | 0 | 3 |
| Endometrioid |  |  |  |  |
| Malignant | 38 | 17 | 21 | 0 |
| LMP | 2 | 2 | 0 | 0 |
| Benign | 0 | 0 | 0 | 0 |
| Other* |  |  |  |  |
| Malignant | 61 | 23 | 29 | 9 |
| LMP | 0 | 0 | 0 | 0 |
| Benign | 5 | 0 | 0 | 5 |

*Other category includes the following tumor types: Brenner's tumor, thecoma, teratoma, fibrothecoma, fibroma, granulosa cell, clear cell, germ cell, mixed mullerian, stromal, undifferentiated, and dysgerminoma.

From the tumor bank, approximately 100 carcinomas were evaluated encompassing most histological sub-types of ovarian carcinoma, including borderline or low-malignant potential tumors and overt carcinomas. The approach included using mRNA prepared from fresh frozen tissue (both normal and malignant) to compare expression of genes in normal, low malignant potential tumors and overt carcinomas. The cDNA prepared from polyA+ mRNA was deemed to be genomic DNA free by checking all preparations with primers that encompassed a known intron-exon splice site using both β-tubulin and p53 primers.

EXAMPLE 7

Northern Blots Analysis

Significant information can be obtained by examining the expression of these candidate genes by Northern blot. Analysis of normal adult multi-tissue blots offers the opportunity to identify normal tissues which may express the protease. Ultimately, if strategies for inhibition of proteases for therapeutic intervention are to be developed, it is essential to appreciate the expression of these genes in normal tissue if and when it occurs.

Northern panels for examining expression of genes in a multi-tissue normal adult as well as fetal tissue are commercially available (CLONTECH). Such evaluation tools are not only important to confirm the overexpression of individual transcripts in tumor versus normal tissues, but also provides the opportunity to confirm transcript size, and to determine if alternate splicing or other transcript alteration may occur in ovarian carcinoma.

Northern blot analysis was performed as follows: 10 μg of mRNA was loaded onto a 1% formaldehyde-agarose gel, electrophoresed and blotted onto a HyBond-N+™ nylon membrane (Amersham). $^{32}$P-labeled cDNA probes were made using Prime-a-Gene Labeling System™ (Promega). The PCR products amplified by specific primers were used as probes. Blots were prehybridized for 30 min and then hybridized for 60 min at 68° C. with $^{32}$P-labeled cDNA probe in ExpressHyb™ Hybridization Solution (CLONTECH). Control hybridization to determine relative gel loading was accomplished using the β-tubulin probe.

Normal human tissues including spleen, thymus, prostate, testis, ovary, small intestine, colon, peripheral blood leukocyte, heart, brain, placenta, lung, liver, skeletal muscle, kidney, pancreas and normal human fetal tissues (Human Multiple Tissue Northern Blot; CLONTECH) were all examined using the same hybridization procedure.

EXAMPLE 8

PCR Products Corresponding to Serine, Cysteine and Metallo-Proteases

Figure 3:
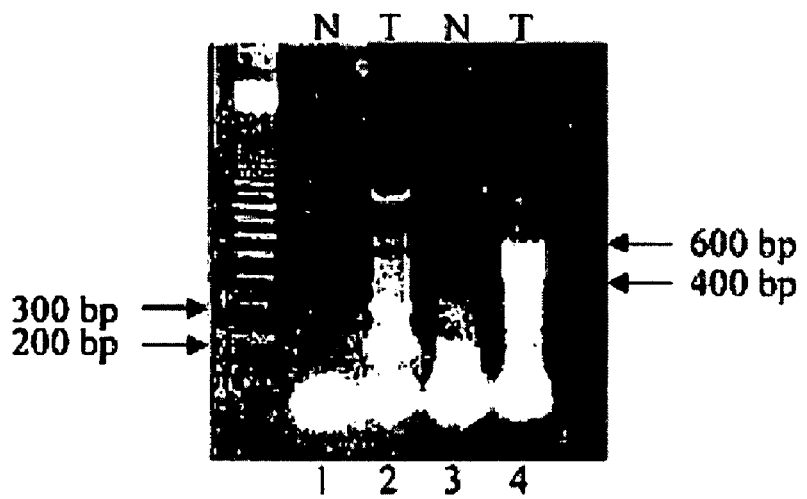
FIG. 3 shows amplification with serine protease redundant primers: histidine sense (S1) with aspartic acid antisense (AS1), using normal cDNA (Lane 1) and tumor cDNA (Lane 2); and histidine sense (S1) with serine antisense (AS2), using normal cDNA (Lane 3) and tumor cDNA (Lane 4).
Figure 4:
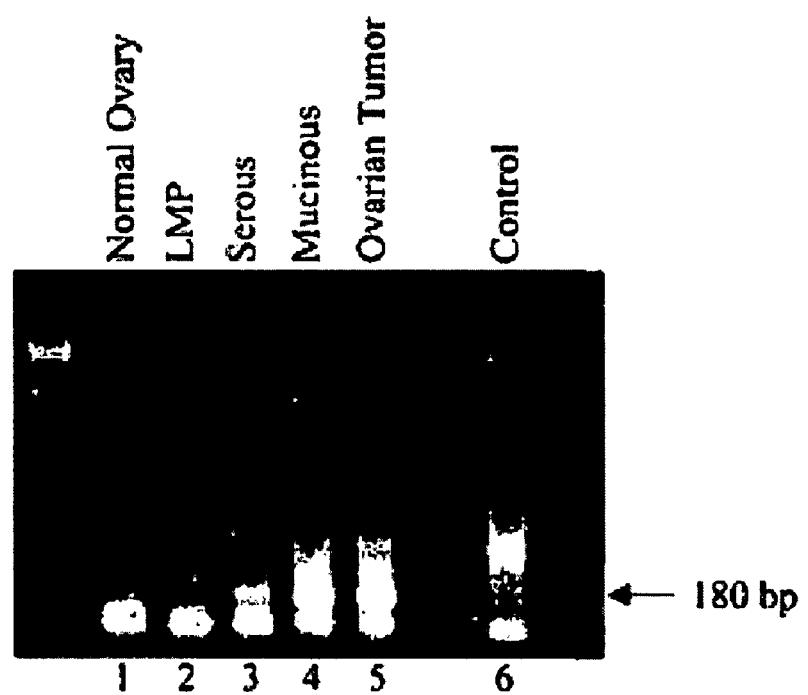
FIG. 4 shows amplification with cysteine protease redundant primers. Normal (Lane 1), low malignant potential (Lane 2), serious carcinoma (Lane 3), mucinous carcinoma (Lane 4), and clear cell carcinoma (Lane 5).
Figure 5:
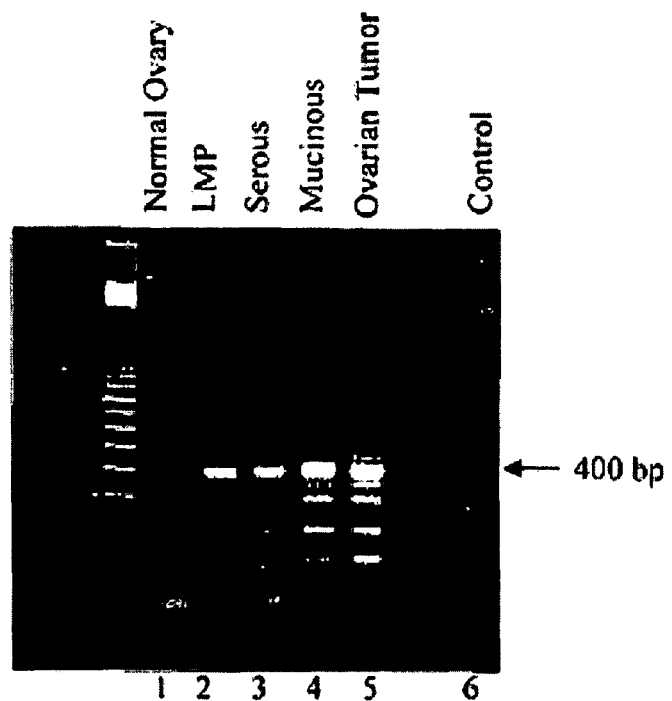
FIG. 5 shows amplification with metallo-protease redundant primers. Normal (Lane 1), low malignant potential (Lane 2), serious carcinoma (Lane 3), mucinous carcinoma (Lane 4), and clear cell carcinoma (Lane 5).

Based on their unique expression in either low malignant potential tumors or carcinomas, PCR-amplified cDNA products were cloned and sequenced and the appropriate gene identified based upon nucleotide and amino acid sequences stored in the GCG and EST databases. FIGS. 3, 4 & 5 show the PCR product displays comparing normal and carcinomatous tissues using redundant primers for serine proteases (FIG. 3), for cysteine proteases (FIG. 4) and for metallo-proteases (FIG. 5). Note the differential expression in the carcinoma tissues versus the normal tissues. The proteases were identified using redundant cDNA primers (Table 2) directed towards conserved sequences that are associated with intrinsic enzyme activity, for serine proteases, cysteine proteases and metallo-proteases, by comparing mRNA expression in normal, low malignant potential and overt ovarian carcinoma tissues according to Sakanari et al. (1989).

EXAMPLE 9

Serine Proteases

For the serine protease group, using the histidine domain primer sense, S1, in combination with antisense primer AS2, the following proteases were identified:

(a) Hepsin, a trypsin-like serine protease cloned from hepatoma cells shown to be a cell surface protease essential for the growth of hepatoma cells in culture and highly expressed in hepatoma tumor cells (FIG. 3, Lane 4);

(b) Complement factor B protease (human factor IX), a protease involved in the coagulation cascade and associated with the production and accumulation of fibrin split products associated with tumor cells (FIG. 3, Lane 4). Compliment factor B belongs in the family of coagulation factors X (Christmas factor). As part of the intrinsic pathway, compliment factor B catalyzes the proteolytic activation of coagulation factor X in the presence of $Ca^{2+}$ phospholipid and factor VIIIa e5; and (c) A stratum corneum chymotryptic enzyme (SCCE) serine protease involved in desquarnation of skin cells from the human stratum corneum (FIG. 3, Lane 4). SCCE is expressed in keratinocytes of the epidermis and functions to degrade the cohesive structures in the cornified layer to allow continuous skin surface shedding.

EXAMPLE 10

Cysteine Proteases

In the cysteine protease group, using redundant sense and anti-sense primers for cysteine proteases, one unique PCR product was identified by overexpression in ovarian carcinoma when compared to normal ovarian tissue (FIG. 4, Lanes 3-5). Cloning and sequencing this PCR product identified a sequence of Cathepsin L which is a lysomal cysteine protease whose expression and secretion is induced by malignant transformation, growth factors and tumor promoters. Many human tumors (including ovarian) express high levels of Cathepsin L. Cathepsin L cysteine protease belongs in the stromolysin family and has potent elastase and collagenase activities. Published data indicates increased levels in the serum of patients with mucinous cystadenocarcinoma of the ovary. It has not heretofore been shown to be expressed in other ovarian tumors.

EXAMPLE 11

Metallo-proteases

Using redundant sense and anti-sense primers for the metallo-protease group, one unique PCR product was detected in the tumor tissue which was absent in normal ovarian tissue (FIG. 5, Lanes 2-5). Subcloning and sequencing this product indicates it has complete homology in the appropriate region with the so-called PUMP-1 (MMP-7) gene. This zinc-binding metallo-protease is expressed as a proenzyme with a signal sequence and is active in gelatin and collagenase digestion. PUMP-1 has also been shown to be induced and overexpressed in 9 of 10 colorectal carcinomas compared to normal colon tissue, suggesting a role for this substrate in the progression of this disease.

EXAMPLE 12 mRNA Expression of SCCE in Ovarian Tumors

Figure 6:
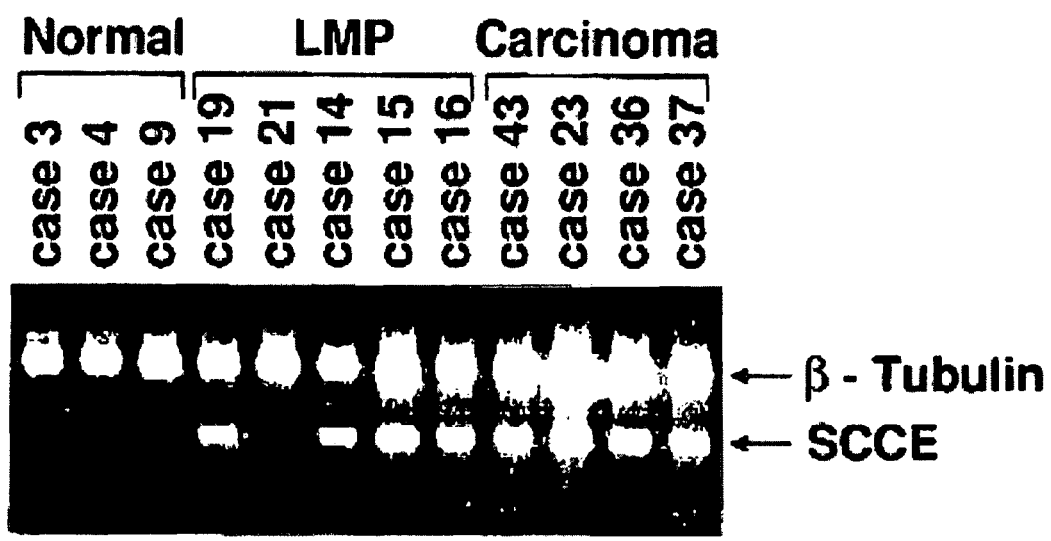
FIG. 6 shows quantitative PCR analysis of SCCE expression. Cases 3, 4 and 9 are normal ovaries. Cases 19, 21, 14, 15 and 16 are LMP tumors. Cases 43, 23, 36 and 37 are ovarian carcinomas. Expression levels of stratum corneum chymotryptic enzyme relative to β-tubulin are significantly elevated in tumor Cases 19, 14, 15, 16, 43, 23, 36 and 37 compared to that of normal ovaries.

To evaluate mRNA expression of SCCE in ovarian tumors, semi-quantitative PCR was performed. A preliminary study confirmed the linearity of the PCR amplification according to the methods of Shigemasa et al. (1997) and Hall et al. (1983). FIG. 6 shows an example of comparative PCR using SCCE primers co-amplified with the internal control β-tubulin primers. Analysis of the data as measured using the phosphoimager and compared as ratios of expression (SCCE/β-tubulin) indicate that SCCE expression is elevated in tumor cases 19, 14, 15, 16, 43, 23, 36 and 37 compared to that of normal ovaries.

Figures 7A, 7B, 7C:
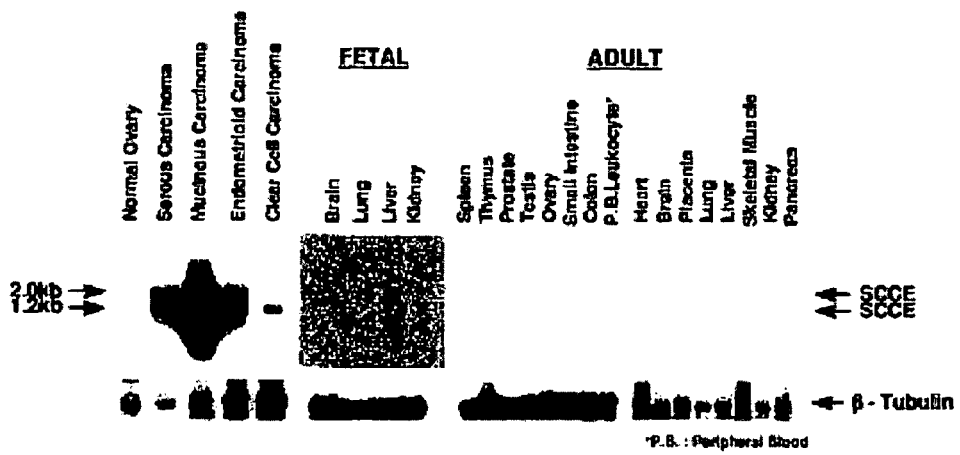
FIG. 7A shows Northern blot analysis of stratum corneum chymotryptic enzyme mRNA from normal ovary and ovarian carcinomas. Lane 1, normal ovary (case 10); Lane 2, serous carcinoma (case 35); Lane 3, mucinous carcinoma (case 48); Lane 4, endometrioid carcinoma (case 51); and Lane 5, clear cell carcinoma (case 54). Two transcripts (1.2 and 2.0 kb) were detected in all of the subtypes of carcinoma (lanes 2-5).
FIGS. 7B and 7C show that normal human adult tissues (spleen, thymus, prostate, testis, ovary, small intestine, colon, peripheral blood leukocyte, heart, brain, placenta, lung, liver, skeletal muscle, kidney and pancreas) and normal human fetal tissues (brain, lung, liver and kidney) examined showed no visible SCCE transcripts.

To confirm the results of the initial quantitative PCR and to examine the size of the transcript, Northern blot hybridization was performed in representative cases of each histological type of carcinoma (FIG. 7A). Northern blot hybridization with a $^{32}$P-labeled SCCE probe (nucleotides 232-570) revealed 1.2 kb and 2.0 kb transcripts, as reported previously in normal skin tissue (Hansson et al., 1994). Those tumor cases which showed overexpression of SCCE by quantitative PCR also showed intense bands of SCCE transcript expression by Northern blot analysis including serous, mucinous, endometrioid and clear cell carcinoma. No transcripts were detected in normal ovarian tissue (Lane 1). Normal human tissues (spleen, thymus, prostate, testis, ovary, small intestine, colon, peripheral blood leukocyte, heart, brain, placenta, lung, liver, skeletal muscle, kidney and pancreas) and normal human fetal tissues (brain, lung, liver and kidney) examined by Northern blot analysis showed no visible SCCE transcripts (FIGS. 7B & 7C). Blots for normal human adult tissues and fetal tissues were subsequently probed to confirm the presence of β-tubulin transcripts.

Figure 8:
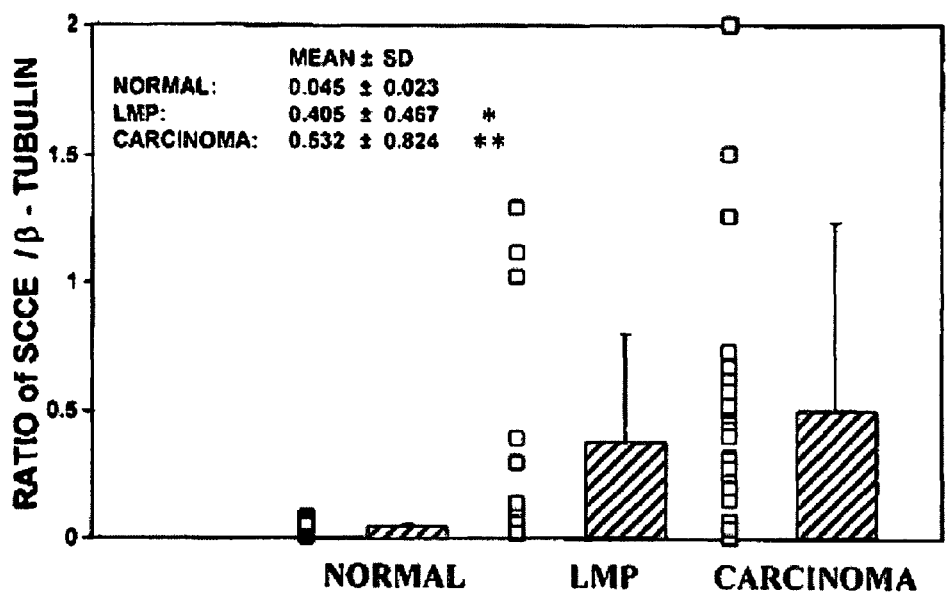
FIG. 8 shows the ratio of SCCE expression to expression of β-tubulin in normal ovary, LMP tumor and ovarian carcinoma. SCCE mRNA expression levels were significantly elevated in LMP tumor ($p<0.05$) and carcinoma ($p<0.001$) compared to that in normal ovary. All 10 cases of normal ovaries showed a low level of SCCE mRNA expression.

Table 5 summarizes the results of the evaluation of SCCE expression in 10 individual normal ovarian tissues and 44 ovarian carcinomas. Overall, SCCE mRNA overexpression (overexpression=mean value for normal ovary+2SD) was found in 8 of 12 LMP tumors (66.7%) and 25 of 32 carcinoma cases (78.1%) with p values of <0.05 and <0.001 respectively (FIG. 8). Overexpression of SCCE transcripts was detected in all ovarian carcinoma subtypes and in both early stage and late stage tumor samples. In the five cases where positive confirmation of lymph node metastasis was identified, all five cases showed overexpression of SCCE at a level of more than four standard deviations above the level for normal ovary. It should be noted that three of these tumors were classified as low malignant potential tumors (all serous adenomas) suggesting a possible relationship between the progression of early stage disease to the lymph when overexpression of SCCE is manifest.

The expression ratio (mean value±SD) for normal ovary was determined as 0.046±0.023, for LMP tumors as 0.405±0.468 and for carcinoma as 0.532±0.824 (Table 6). From a histological point of view, overexpression of SCCE was observed in 23 of 26 serous tumors (88.5%) including 6 of 7 LMP tumors and 17 of 19 carcinomas. However only 4 of 12 mucinous tumors (33.3%) including 2 of 5 LMP tumors and 2 of 7 carcinomas showed overexpression of SCCE. For endometrioid and clear cell carcinoma, stratum corneum chymotryptic enzyme was found to be overexpressed in all 6 cases (Table 6).

TABLE 5

Patient Characteristics and Expression of SCCE Gene

| Case | Histological Type[a] | Stage/Grade | LN[b] | mRNA expression[c] SCCE |
|---|---|---|---|---|
| 1 | normal ovary | | | n |
| 2 | normal ovary | | | n |
| 3 | normal ovary | | | n |
| 4 | normal ovary | | | n |
| 5 | normal ovary | | | n |
| 6 | normal ovary | | | n |
| 7 | normal ovary | | | n |
| 8 | normal ovary | | | n |
| 9 | normal ovary | | | n |
| 10 | normal ovary | | | n |
| 11 | s adenoma (LMP) | 1/1 | n | 4+ |
| 12 | s adenoma (LMP) | 1/1 | NE | n |
| 13 | s adenoma (LMP) | 1/1 | NE | 2+ |
| 14 | s adenoma (LMP) | 1/1 | n | 4+ |
| 15 | s adenoma (LMP) | 3/1 | p | 4+ |
| 16 | s adenoma (LMP) | 3/1 | p | 4+ |
| 17 | s adenoma (LMP) | 3/1 | p | 4+ |
| 18 | m adenoma (LMP) | 1/1 | NE | 4+ |
| 19 | m adenoma (LMP) | 1/1 | n | 4+ |
| 20 | m adenoma (LMP) | 1/1 | n | n |
| 21 | m adenoma (LMP) | 1/1 | NE | n |
| 22 | m adenoma (LMP) | 1/1 | NE | n |
| 23 | s carcinoma | 1/2 | n | 4+ |
| 24 | s carcinoma | 1/3 | n | 4+ |
| 25 | s carcinoma | 3/1 | NE | 4+ |
| 26 | s carcinoma | 3/2 | NE | 4+ |
| 27 | s carcinoma | 3/2 | p | 4+ |
| 28 | s carcinoma | 3/2 | NE | 4+ |
| 29 | s carcinoma | 3/3 | NE | 4+ |
| 30 | s carcinoma | 3/3 | NE | 4+ |
| 31 | s carcinoma | 3/3 | NE | 4+ |
| 32 | s carcinoma | 3/3 | NE | 4+ |
| 33 | s carcinoma | 3/3 | n | 4+ |
| 34 | s carcinoma | 3/3 | NE | n |
| 35 | s carcinoma | 3/3 | NE | 4+ |
| 36 | s carcinoma | 3/3 | NE | 4+ |
| 37 | s carcinoma | 3/3 | NE | 4+ |
| 38 | s carcinoma | 3/3 | n | 4+ |
| 39 | s carcinoma | 3/2 | NE | 4+ |
| 40 | s carcinoma | 3/3 | NE | 4+ |
| 41 | s carcinoma | 3/2 | NE | n |

TABLE 5-continued

Patient Characteristics and Expression of SCCE Gene

| Case | Histological Type[a] | Stage/Grade | LN[b] | mRNA expression[c] SCCE |
|---|---|---|---|---|
| 42 | m carcinoma | 1/2 | n | n |
| 43 | m carcinoma | 2/2 | NE | 4+ |
| 44 | m carcinoma | 2/2 | n | n |
| 45 | m carcinoma | 3/1 | NE | n |
| 46 | m carcinoma | 3/2 | NE | n |
| 47 | m carcinoma | 3/2 | NE | n |
| 48 | m carcinoma | 3/3 | NE | 4+ |
| 49 | e carcinoma | 2/3 | n | 4+ |
| 50 | e carcinoma | 3/2 | NE | 4+ |
| 51 | e carcinoma | 3/3 | NE | 4+ |
| 52 | c carcinoma | 1/3 | n | 4+ |
| 53 | c carcinoma | 1/1 | n | 4+ |
| 54 | c carcinoma | 3/2 | p | 4+ |

[a]s; serous, m; mucinous, e; endometrioid, c; clear cell;
[b]LN; lymph node metastasis, p; positive, n; negative, NE; not examined;
[c]n, normal range is equal to Mean ± 2SD, 2+; Mean + 2SD to + 4SD, 4+; Mean + 4SD or greater

TABLE 6

Overexpression of SCCE in Ovarian Carcinoma

| | N | Overexpression of SCCE | Expression Ratio[a] |
|---|---|---|---|
| Normal | 10 | 0 (0%) | 0.046 ± 0.023 |
| LMP | 12 | 8 (66.7%) | 0.045 ± 0.468 |
| serous | 7 | 6 (85.7%) | 0.615 ± 0.518 |
| mucinous | 5 | 2 (40.0%) | 0.111 ± 0.117 |
| Carcinomas | 32 | 25 (78.1%) | 0.532 ± 0.824 |
| serous | 19 | 17 (89.9%) | 0.686 ± 1.027 |
| mucinous | 7 | 2 (28.6%) | 0.132 ± 0.265 |
| endometriod | 3 | 3 (100%) | 0.511 ± 0.205 |
| clear cell | 3 | 3 (100%) | 0.515 ± 0.007 |

[a]The ratio of expression level of SCCE to β-tubulin

EXAMPLE 13

Western Blot Analysis

Polyclonal rabbit antibodies were generated by immunization with a combination of 2 poly-lysine linked multiple Ag peptides derived from SCCE protein sequences PLQILLLSLALE (SEQ ID NO: 28) and SFRHPGYSTQTH (SEQ ID NO: 29). Approximately 20 ng of MDA-MBA-435S and HeLa cell lysates were separated on a 15% SDS-PAGE gel and electroblotted to PVDF at 100 V for 40 minutes at 4° C. The proteins were fixed to the membrane by incubation in 50% MeOH for 10 minutes. The membrane was blocked overnight in TBS, pH 7.8 containing 0.2% non-fat milk. Primary antibody was added to the membrane at a dilution of 1:100 in 0.2% milk/TBS and incubated for 2 hours at room temperature. The blot was washed and incubated with a 1:3000 dilution of alkaline-phosphatase conjugated goat anti-rabbit IgG (BioRad) for one hour at room temperature. The blot was washed and incubated with a chemiluminescent substrate before a 10 second exposure to X-ray film for visualization.

Figure 9:
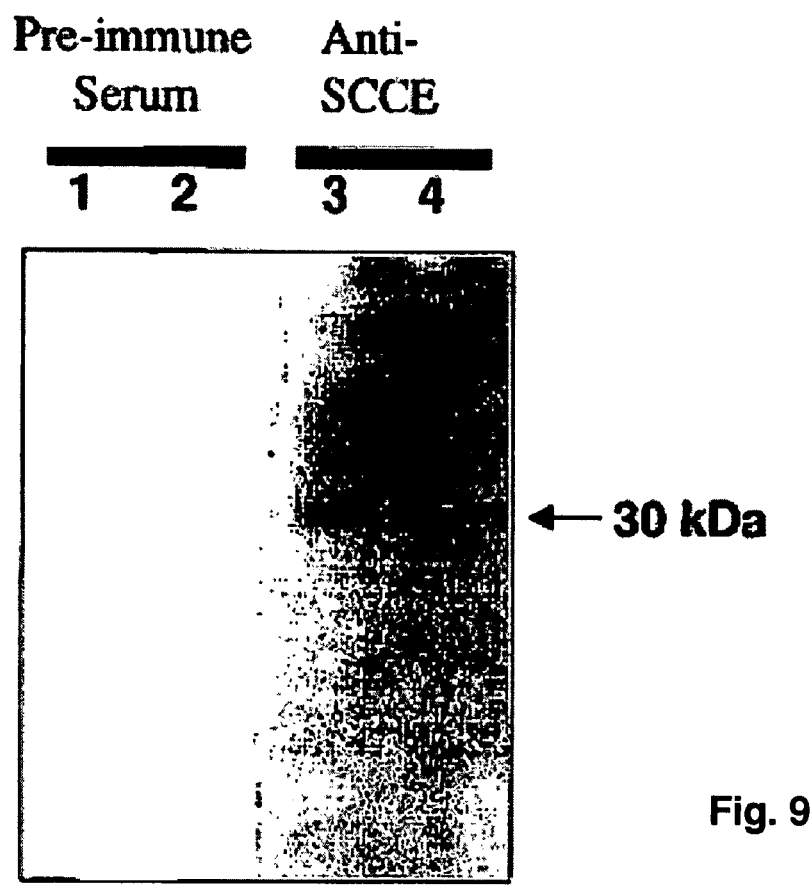
FIG. 9 shows MDA-MB-435S (Lanes 1 & 3) and HeLa (Lanes 2 & 4) cell lysates were separated by SDS-PAGE and immunoblotted. Lanes 1 & 2 were probed with rabbit preimmune serum as a negative control. Lanes 3 & 4 were probed with polyclonal rabbit antibodies generated to peptides derived from SCCE protein sequence.

Two cell lines HeLa and MDA-MB-435S previously shown to express mRNA transcripts were examined by Western blot to confirm the presence of SCCE protein. FIG. 9 indicates that polyclonal antibodies developed to peptides (12 mers bound to polylysine) derived from the amino and carboxy termini of SCCE bind a protein of approximately 30 kDa in cytosolic extracts of HeLa and MDA-MB435S cells. The ovarian tumor cell line CAOV3 was also examined for SCCE expression and a protein product could not be detected (data not shown). This molecular size protein agrees with the anticipated and known parameters for the SCCE protein. It should be noted that only a single band was detected by Western blot analysis of cytosolic protein. It might be anticipated that the SCCE protein prior to secretion would be present in the inactivated parent form i.e. the seven amino terminal peptide removed on activation would still be present on the enzyme. In this pre-active form of the enzyme it would be anticipated that the apparent molecular weight on Western blot would be about 30 kDa.

EXAMPLE 14

Immunohistochemistry

Immunohistochemical localization of SCCE antigen was examined using normal ovaries, mucinous LMP tumor and adenocarcinomas (including serous adenocarcinomas, mucinous adenocarcinoma and clear cell carcinomas) in the same series of the samples for mRNA isolation. Formalin fixed and paraffin embedded sections, 4 μm thick, were cut and mounted on aminopropyltriethoxysilane treated slides. Slides were routinely deparaffinized with xylene and rehydrated with a series of ethanol washes. Nonenzymatic antigen retrieval was performed by processing using microwave heat treatment in 0.01 M sodium citrate buffer (pH 6.0). Immunohistochemical staining was performed manually using the avidin-biotin peroxidase complex technique (Vectastain Elite ABC kit, Vector Laboratories). Anti-SCCE rabbit polyclonal antibody was generated by immunization with a combination of 2 poly-lysine linked multiple Ag peptide derived from the SCCE protein-sequences.

This indirect immunoperoxidase staining procedure was performed at room temperature. Endogenous peroxidase and nonspecific background staining were blocked by incubating slides with methanol with 0.3% $H_2O_2$ for 30 minutes. After washing with phosphate-buffered saline (PBS) for 10 minutes, sections were incubated with biotinylated anti-rabbit IgG for 30 minutes. After washing with PBS for 10 minutes, slides were incubated with ABC reagent for 30 minutes. The final products were visualized by using AEC substrate system (DAKO Corporation) and sections were counterstained with Mayer hematoxylin for 20 seconds before mounting. Positive controls and negative controls were used for each section. Negative controls were performed by using normal rabbit serum instead of the primary antibody. All experiments were duplicated. The stained slides were examined microscopically by 3 observers. More than 10% of positive tumor cells was the criterion for a 1+ positive staining and more than 50% of positive tumor cells was the criterion for a 2+ positive staining.

To further confirm the presence of the SCCE protein in ovarian tumor cells as opposed to its elaboration by supporting stromal or blood vessel cells, both normal ovarian epithelia and ovarian tumor tissue were examined by immunohistochemistry using the polyclonal antiserum described above. All 14 ovarian tumors showed positive staining of SCCE, whereas normal ovarian surface epithelium showed very weak expression of SCCE antigen (FIG. 10A). 8 of 10 serous adenocarcinomas, 1 of 1 mucinous adenocarcinoma, and 2 of 2 clear cell carcinomas showed 2+ positive staining (more than 50% of positive tumor cells) of SCCE (Table 7). FIGS. 10C and 10E show that stratum corneum chymotryptic enzyme staining is localized to the cytoplasm and the cell membrane of ovarian tumor cells. The negative control of each case was also performed, wherein the result showed no nonspecific staining of stratum corneum chymotryptic enzyme (FIGS. 10B, 10D and 10F). Staining of normal ovarian epithelial cells showed little SCCE expression (FIG. 10A).

TABLE 7

Immunohistochemical Expression of SCCE Protein in Normal Ovary and Ovarian Tumor

| Lab NO: | Histology | SCCE |
|---|---|---|
|  | normal ovary | weak + |
|  | normal ovary | weak + |
|  | normal ovary | weak + |
|  | normal ovary | weak + |
|  | normal ovary | weak + |
|  | normal ovary | weak + |
| 1036 | mucinous LMP | + |
| 475 | serous carcinoma | + |
| 465 | serous carcinoma | ++ |
| 464 | serous carcinoma | ++ |
| 1039 | serous carcinoma | ++ |
| 960 | serous carcinoma | ++ |
| 962 | serous carcinoma | ++ |
| 1551 | serous carcinoma | ++ |
| 1813 | serous carcinoma | ++ |
| 1817 | serous carcinoma | + |
| 1819 | serous carcinoma | ++ |
| 1244 | mucinous carcinoma | ++ |
| 947 | clear cell carcinoma | ++ |
| 948 | clear cell carcinoma | ++ |

EXAMPLE 15

Summary of Proteases Detected Herein

Most of the above-listed proteases were identified from the sense-His/antisense-Ser primer pair, yielding a 500 bp PCR product (FIG. 1, Lane 4). Some of the enzymes are familiar, a short summary of each follows.

Hepsin

Hepsin is a trypsin-like serine protease cloned from hepatoma cells. Hepsin is an extracellular protease (the enzyme includes a secretion signal sequence) which is anchored in the plasma membrane by its amino terminal domain, thereby exposing its catalytic domain to the extracellular matrix. Hepsin has also been shown to be expressed in breast cancer cell lines and peripheral nerve cells. Hepsin has never before been associated with ovarian carcinoma. Specific primers for the hepsin gene were synthesized and the expression of hepsin examined using Northern blots of fetal tissue and ovarian tissue (both normal and ovarian carcinoma).

Figures 11A, 11B, 11C:
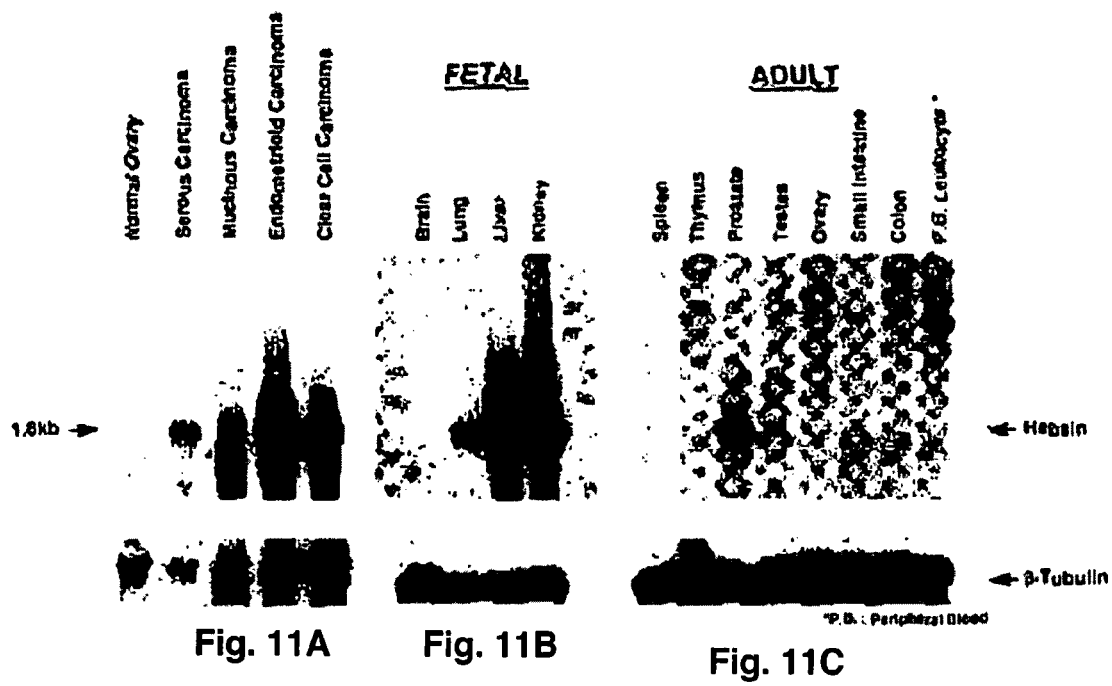
FIG. 11A shows Northern blot analysis of hepsin expression in normal ovary and ovarian carcinomas. Lane 1, normal ovary (case 10); lane 2, serous carcinoma (case 35); lane 3, mucinous carcinoma (case 48); lane 4, endometrioid carcinoma (case 51); and lane 5, clear cell carcinoma (case 54). In cases 35, 51 and 54, more than a 10-fold increase in the hepsin 1.8 kb transcript abundance was observed. Northern blot analysis of hepsin in normal human fetal (FIG. 11B) and adult tissues (FIG. 11C). Significant overexpression of the hepsin transcript is noted in both fetal liver and fetal kidney. Notably, hepsin overexpression is not observed in normal adult tissue. Slight expression above the background level is observed in the adult prostate.

FIG. 11A shows that hepsin was expressed in ovarian carcinomas of different histologic types, but not in normal ovary. FIG. 11B shows that hepsin was expressed in fetal liver and fetal kidney as anticipated, but at very low levels or not at all in fetal brain and lung. FIG. 11C shows that hepsin overexpression is not observed in normal adult tissue. Slight expression above the background level is observed in the adult prostate. The mRNA identified in both Northern blots was the appropriate size for the hepsin transcript.

Figure 12A:
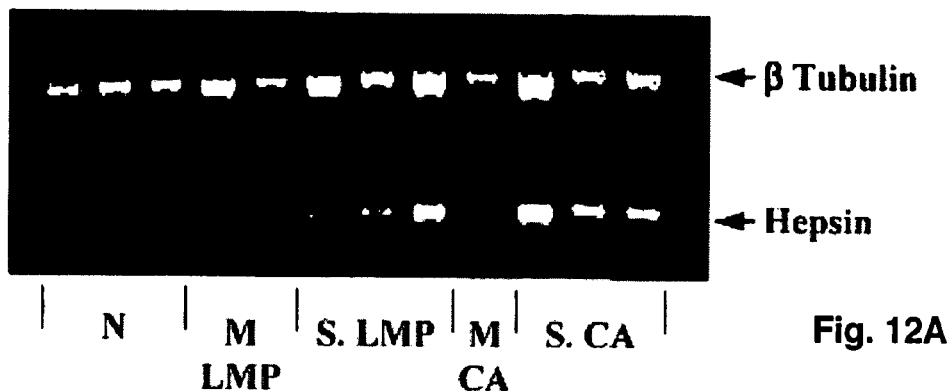
FIG. 12A shows hepsin expression in normal (N), mucinous (M) and serous (S) low malignant potential (LMP) tumors and carcinomas (CA).
Figure 12B:
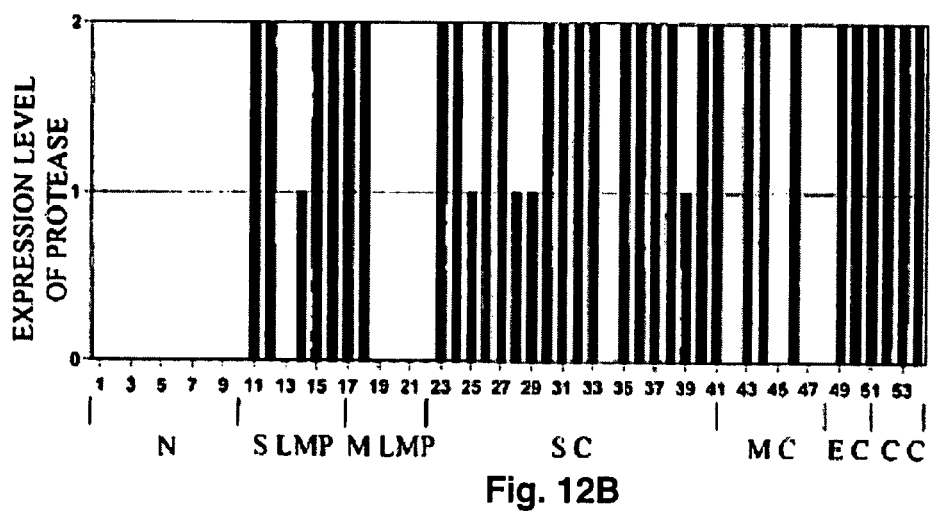
FIG. 12B shows a bar graph of expression of hepsin in 10 normal ovaries and 44 ovarian carcinoma samples. 0:<Mean+2SD; i:>Mean+2SD<4SD; 2::>Mean+4SD.

The expression of hepsin was examined in 10 normal ovaries and 44 ovarian tumors using specific primers to β-tubulin and hepsin in a quantitative PCR assay. Expression is presented as the ratio of $^{32}$P-hepsin band to the internal control, the $^{32}$P-β-3-tubulin band. Hepsin mRNA is highly overexpressed in most histopathologic types of ovarian carcinomas including some low malignant potential tumors (see FIGS. 12A & 12B). Most noticeably, hepsin is highly expressed in serous, endometrioid and clear cell tumors tested. It is highly expressed in some mucinous tumors, but it is not overexpressed in the majority of such tumors.

Stratum Corneum Chymotrypsin Enzyme (SCCE)

The PCR product identified was the catalytic domain of the sense-His/antisense-Ser of the SCCE enzyme. This extracellular protease was cloned, sequenced and shown to be expressed on the surface of keratinocytes in the epidermis. SCCE is a chymotrypsin-like serine protease whose function is suggested to be in the catalytic degradation of intercellular cohesive structures in the stratum corneum layer of the skin. This degradation allows continuous shedding (desquamation) of cells from the skin surface. The subcellular localization of SCCE is in the upper granular layer in the stratum corneum of normal non-palmoplantar skin and in the cohesive parts of hypertrophic plantar stratum corneum. SCCE is exclusively associated with the stratum corneum and has not been shown to be expressed in any carcinomatous tissues.

Northern blots were probed with the PCR product to determine expression of SCCE in fetal tissue and ovarian carcinoma (FIGS. 7A, 7B and 7C). Noticeably, detection of SCCE messenger RNA on the fetal Northern was almost non-existent (a problem with the probe or the blot was excluded by performing the proper controls). A faint band appeared in fetal kidney. On the other hand, SCCE mRNA is abundant in the ovarian carcinoma mRNA (FIG. 7A). Two transcripts of the correct size are observed for SCCE. The same panel of cDNA used for SCCE analysis was used for SCCE expression.

No SCCE expression was detected in the normal ovary lane of the Northern blot. A comparison of all candidate genes, including a loading marker (β-tubulin), was shown to confirm that this observation was not a result of a loading bias. Quantitative PCR using SCCE primers, along with β-tubulin internal control primers, confirmed the overexpression of SCCE mRNA in carcinoma of the ovary with no expression in normal ovarian tissue (FIG. 6). FIG. 8 shows the ratio of SCCE to the β-tubulin internal standard in 10 normal and 44 ovarian carcinoma tissues. Again, it is observed that SCCE is highly overexpressed in ovarian carcinoma cells. It is also noted that some mucinous tumors overexpress SCCE, but the majority do not.

Protease M

Figures 13, 14:
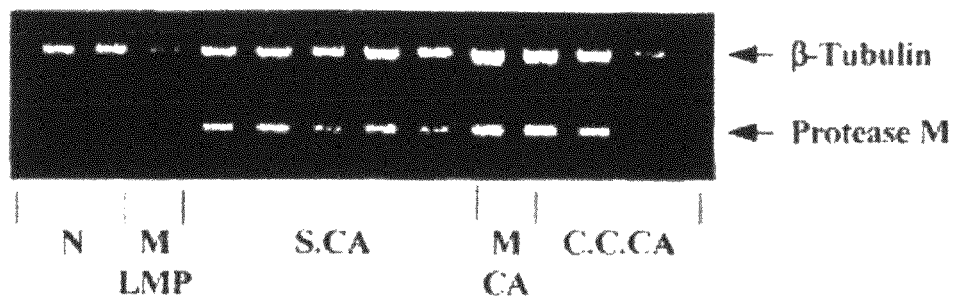
FIG. 13 shows a comparison by quantitative PCR of normal and ovarian carcinoma expression of mRNA for protease M.
FIG. 14 shows TADG-12 catalytic domain with an insert near the His 5'-end.

Protease M was identified from subclones of the His-ser primer pair. This protease was cloned by Anisowicz, et al., and shown to be overexpressed in carcinomas. A evaluation indicates that this enzyme is overexpressed in ovarian carcinoma (FIG. 13).

Cofactor I and Complement Factor B

Several serine proteases associated with the coagulation pathway were also subcloned. Examination of normal and ovarian carcinomas by quantitative PCR for expression of these enzymes, it was noticeable that this mRNA was not clearly overexpressed in ovarian carcinomas when compared to normal ovarian tissue. It should be noted that the same panel of tumors was used for the evaluation of each candidate protease.

EXAMPLE 16

Summary of Previously Unknown Proteases Detected Herein

TADG-12

TADG-12 was identified from the primer pairs, sense-His/antisense-Asp (see FIG. 1, Lanes 1 & 2). Upon subcloning both PCR products in lane 2, the 200 bp product had a unique protease-like sequence not included in GenBank. This 200 bp product contains many of the conserved amino acids common for the His-Asp domain of the family of serine proteins. The second and larger PCR product (300 bp) was shown to have a high degree of homology with TADG-12 (His-Asp sequence), but also contained approximately 100 bp of unique sequence. Synthesis of specific primers and the sequencing of the subsequent PCR products from three different tumors demonstrated that the larger PCR product (present in about 50% of ovarian carcinomas) includes an insert of about 100 bp near the 5' end (and near the histidine) of the sequence. This insert may be a retained genomic intron because of the appropriate position of splice sites and the fact that the insert does not contain an open reading frame (see FIG. 14). This suggests the possibility of a splice site mutation which gives rise to retention of the intron, or a translocation of a sequence into the TADG-12 gene in as many as half of all ovarian carcinomas.

TADG-13 and TADG-14

Figure 15A:
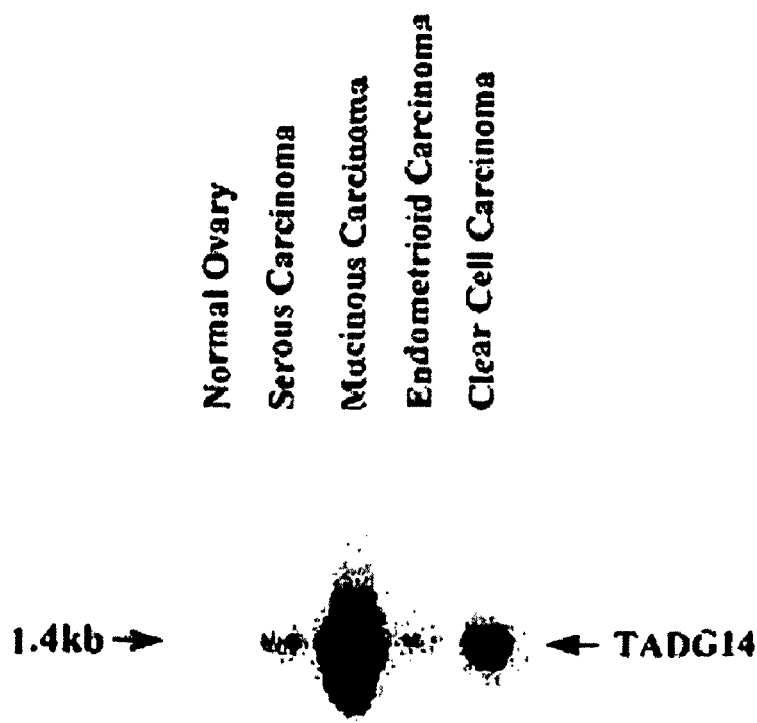
FIG. 15A shows northern blot analysis comparing TADG-14 expression in normal and ovarian carcinoma tissues.
Figure 15B:
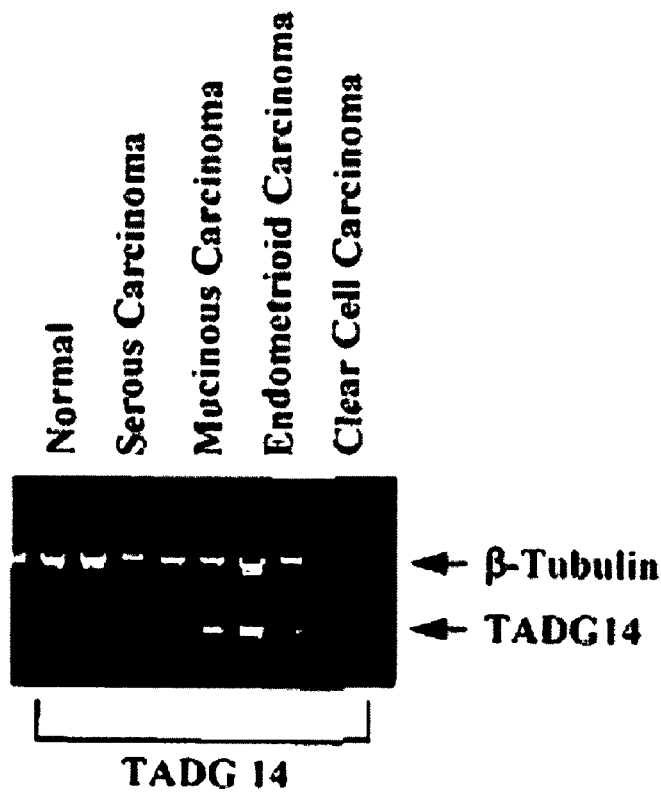
FIG. 15B shows preliminary quantitative PCR amplification of normal and carcinoma cDNAs using specific primers for TADG-14.

Specific primers were synthesized for TADG-13 and TADG-14 to evaluate expression of genes in normal and ovarian carcinoma tissue. Northern blot analysis of ovarian tissues indicates the transcript for the TADG-14 gene is approximately 1.4 kb and is expressed in ovarian carcinoma tissues (FIG. 15A) with no noticeable transcript presence in normal tissue. In quantitative PCR studies using specific primers, increased expression of TADG-14 in ovarian carcinoma tissues was noted compared to a normal ovary (FIG. 15B). The presence of a specific PCR product for TADG-14 in both an HeLa library and an ovarian carcinoma library was also confirmed. Several candidate sequences corresponding to TADG-14 have been screened and isolated from the HeLa library.

Clearly from sequence homology, these genes fit into the family of serine proteases. TADG-13 and TADG-14 are, however, heretofore undocumented genes which the specific primers of the invention allow to be evaluated in normal and tumor cells, and with which the presence or absence of expression of these genes is useful in the diagnosis or treatment selection for specific tumor types.

PUMP-1

In a similar strategy using redundant primers to metal binding domains and conserved histidine domains, a differentially expressed PCR product identical to matrix metalloprotease 7 (MMP-7) was identified, herein called PUMP-1. Using specific primers for PUMP-1, PCR produced a 250 bp product for Northern blot analysis.

Figures 16A, 16B, 16C:
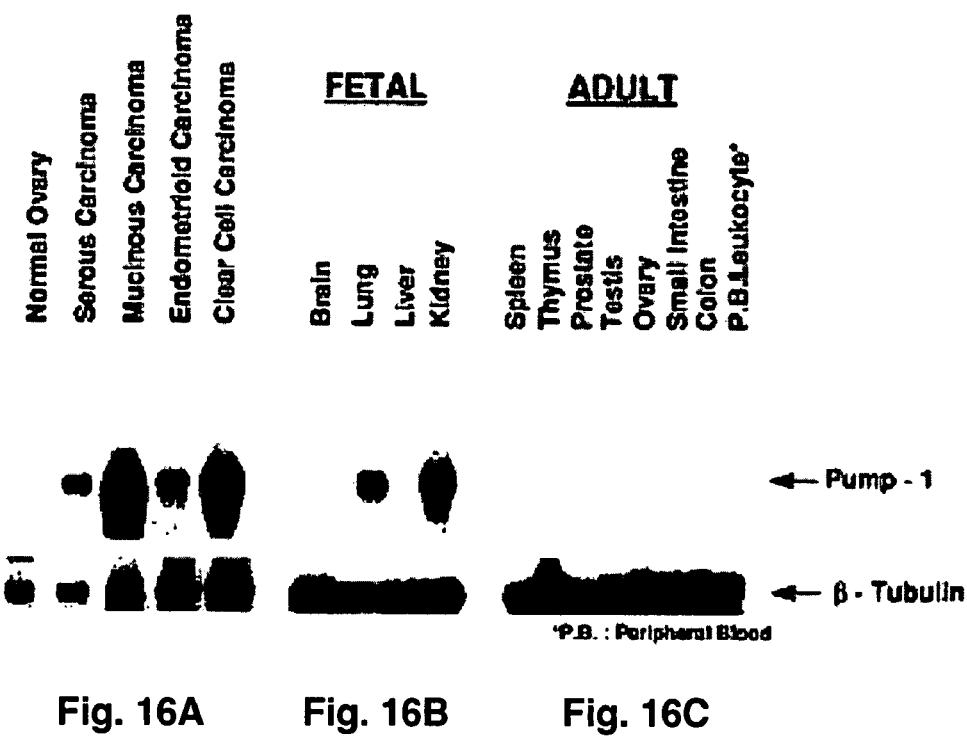
FIG. 16A shows northern blot analysis of the PUMP-1 gene in normal ovary and ovarian carcinomas.
FIG. 16B shows northern blot analysis of the PUMP-1 gene in human fetal tissue.
FIG. 16C shows northern blot analysis of the PUMP-1 gene in adult tissues.
Figure 17A:
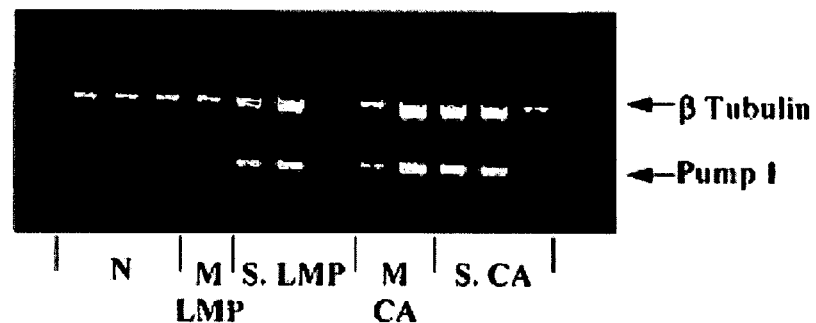
FIG. 17A shows a comparison of PUMP-1 expression in normal and carcinoma tissues using quantitative PCR with an internal β-tubulin control.
Figure 17B:
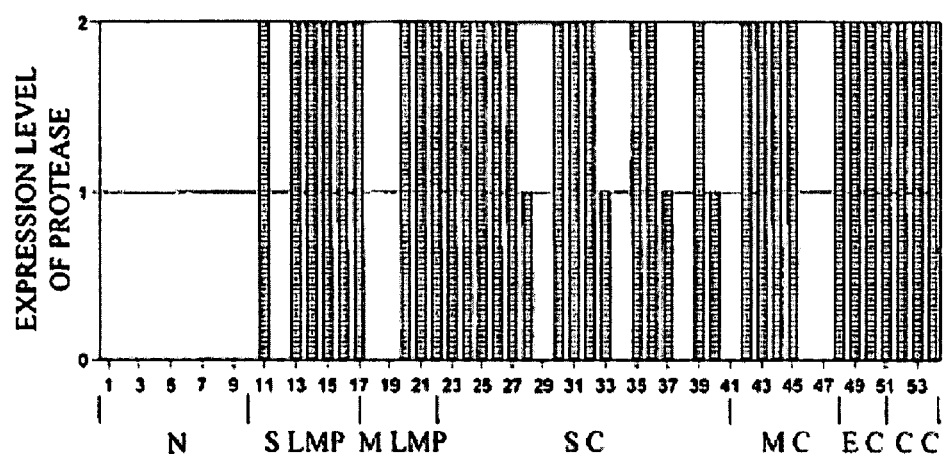
FIG. 17B shows the ratio of mRNA expression of PUMP-1 compared to the internal control β-tubulin in 10 normal and 44 ovarian carcinomas. SD is as in FIG. 12B.

MMP-7 or PUMP-1 is differentially expressed in fetal lung and kidney tissues. FIG. 16A compares PUMP-1 expression in normal ovary and carcinoma subtypes using Northern blot analysis. Notably, PUMP-1 is expressed in ovarian carcinoma tissues, and again, the presence of a transcript in normal tissue was not detected. FIG. 16B shows the expression of PUMP-1 in human fetal tissue, while no transcript could be detected in either fetal brain or fetal liver. FIG. 16C shows that PUMP-1 overexpression is not observed in normal adult tissue. Quantitative PCR comparing normal versus ovarian carcinoma expression of the PUMP-1 mRNA indicates that this gene is highly expressed in serous carcinomas, including most low malignant serous tumors, and is, again, expressed to a lesser extent in mucinous tumors (FIGS. 17A & 17B). PUMP-1, however, is so far the protease most frequently found overexpressed in mucinous tumors (See Table 8 below).

Cathepsin-L

Figure 18:
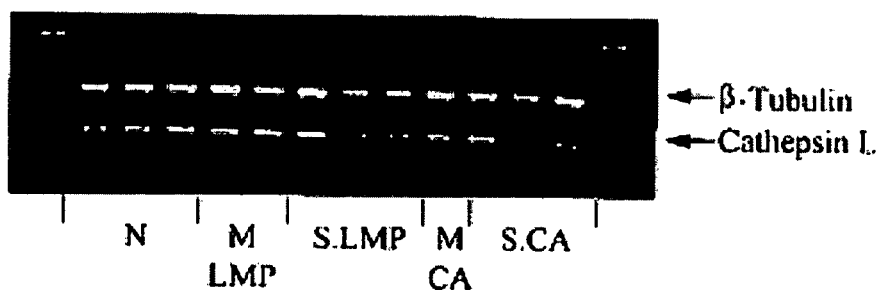
FIG. 18 shows a comparison of Cathepsin L expression in normal and carcinoma tissues using quantitative PCR with an internal β-tubulin control.

Using redundant cysteine protease primers to conserved domains surrounding individual cysteine and histidine residues, the cathepsin-L protease was identified in several serous carcinomas. An initial examination of the expression of cathepsin L in normal and ovarian tumor tissue indicates that transcripts for the cathepsin-L protease are present in both normal and tumor tissues (FIG. 18). However, its presence or absence in combination with other proteases of the present invention permits identification of specific tumor types and treatment choices.

Conclusion

Figure 19:
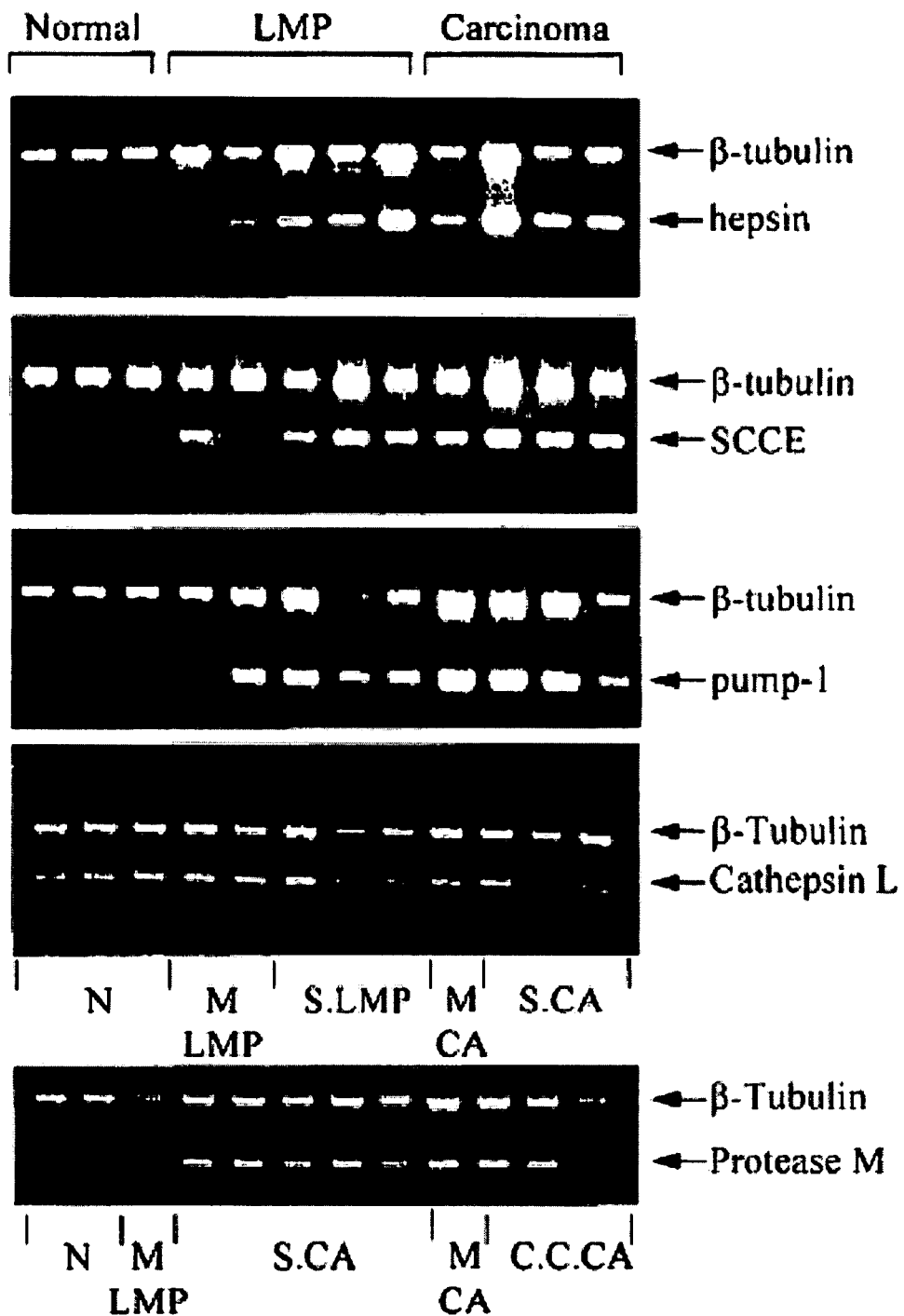
FIG. 19 is a summary of PCR amplified products for the hepsin, SCCE, protease M, PUMP-1 and Cathepsin L genes.

Redundant primers to conserved domains of serine, metallo-, and cysteine proteases have yielded a set of genes whose mRNAs are overexpressed in ovarian carcinoma. The genes which are clearly overexpressed include the serine proteases hepsin, SCCE, protease M, TADG12, TADG14 and the metallo-protease PUMP-1 (see FIG. 19 and Table 8). Northern blot analysis of normal and ovarian carcinoma tissues indicated overexpression of hepsin, SCCE, PUMP-1 and TADG-14. A β-tubulin probe to control for loading levels was included.

TABLE 8

| Overexpression of Proteases in Ovarian Tumors | | | | | |
|---|---|---|---|---|---|
| Type | N | Hepsin | SCCE | Pump-1 | Protease M |
| Normal | 10 | 0% (0/10) | 0% (0/10) | 0% (0/10) | 0% (0/10) |
| LMP | 12 | 58.3% (7/12) | 66.7% (8/12) | 75.0% (9/12) | 75% (9/12) |
| serous | 7 | 85.7% (6/7) | 85.7% (6/7) | 85.7% (6/7) | 100% (7/7) |
| mucinous | 5 | 20.0% (1/5) | 40.0% (2/5) | 60% (3/5) | 40.0% (2/5) |
| Carcinoma | 32 | 84.4% (27/32) | 78.1% (25/32) | 81.3% (26/32) | 90.6% (29/32) |
| serous | 19 | 94.7% (18/19) | 89.5% (17/19) | 78.9% (15/19) | 94.7% (18/19) |
| mucinous | 7 | 42.9% (3/7) | 28.6% (2/7) | 71.4% (5/7) | 85.7% (6/7) |
| endometr. | 3 | 100% (3/3) | 100% (3/3) | 100% (3/3) | 100% (3/3) |
| clear cell | 3 | 100% (3/3) | 100% (3/3) | 100% (3/3) | 67.7% (2/3) |

Discussion

For the most part, these proteins previously have not been associated with the extracellular matrix of ovarian carcinoma cells. No panel of proteases which might contribute to the growth, shedding, invasion and colony development of metastatic carcinoma has been previously described, including the three new candidate serine proteases which are herein disclosed. The establishment of an extracellular protease panel associated with either malignant growth or malignant potential offers the opportunity for the identification of diagnostic or prognostic markers and for therapeutic intervention through inhibition or down regulation of these proteases.

The availability of the instant gene-specific primers coding for the appropriate region of tumor specific proteases allows for the amplification of a specific cDNA probe using Northern and Southern analysis, and their use as markers to detect the presence of the cancer in tissue. The probes also allow more extensive evaluation of the expression of the gene in normal ovary versus low malignant potential tumor, as well as both high- and low-stage carcinomas. The evaluation of a panel of fresh frozen tissue from all the carcinoma subtypes (Table 4) allowed the determination of whether a protease is expressed predominantly in early stage disease or within specific carcinoma subtypes. It was also determined whether each gene's expression is confined to a particular stage in tumor progression and/or is associated with metastatic lesions. Detection of specific combinations of proteases is an identifying characteristic of the specific tumor types and yields valuable information for diagnoses and treatment selection. Particular tumor types may be more accurately diagnosed by the characteristic expression pattern of each specific tumor.

Specifically, the present invention utilizes primers to the conserved catalytic triad domain of the serine protease family (viz. His-Asp-Ser). Using such a strategy to display serine protease transcripts found in abundance in carcinoma tissues, with little or no expression in normal ovary, SCCE gene was detected.

The overall expectation of the search was to identify cell surface or secreted products which may promote either tumor growth or metastasis. Confirmation of the presence of SCCE (a secreted serine protease) in ovarian tumors was indicated initially by subcloning and sequencing PCR products derived from amplification of tumor cDNA using redundant primes to the histidine (sense) and the serine (antisense) conserved domains of the serine protease catalytic sequences. Characterization of the SCCE protease (Egelrud, 1993) indicated that the cohesion between individual corneocytes in the stratum corneurn, the primary substrate for cellular desquamation or shedding of skin cells may be degraded by SCCE. Proteolysis of these intercellular matrices is one of the major events preceding desquamation. SCCE has only been identified in the stratum corneurn (Egelrud, 1993; Hansson et al., 1994) and immunohistochemical studies confirmed its unique tissue specific expression by the epithelial cells of the stratum corneurn (Sondell et al., 1994). It was therefore surprising to discover that this highly conserved expression of SCCE to skin is obviated when transformation and carcinogenesis of ovarian epithelial cells occurs. The clearly distinctive pattern of expression in both low malignant potential tumors and overt carcinomas of the ovary over normal ovarian tissue suggests that the SCCE protease may also play a role in shedding or desquamation of ovarian tumor cells. This association is especially well preserved in serous adenocarcinomas where disease progression is characterized by early foci of peritoneal metastasis and which may be the result of an early overexpression of enzymes such as SCCE and consequent tumor cell shedding. Because SCCE and other proteases (e.g. hepsin) are overexpressed in ovarian tumors (again with particularly high overexpression in serous tumors), it seems likely that a concert of lytic activity at the cell surface may be involved in malignant potential. Several aspects of the tumorigenic process can be dissected and identified as component parts of such a surface protease concert viz 1) initial expansion of newly transformed cells into the surrounding matrix of supporting tissue of the primary organ; 2) desquamation or shedding of tumor cells into the surrounding environment; 3) invasion of basement membrane of the target organ of metastasis; and 4) activation of mitogenic and angiogenic factors to support the newly established metastatic colony.

While it is not yet clear which proteases are the primary agents in each of these malignant progression steps, the data here indicate the potential for the involvement of SCCE in the shedding or desquamation phase of this progression. Certain other factors remain to be resolved even with regard to SCCE involvement in tumor cell shedding which include activation of SCCE by proteolysis or cleaving of the aminoterminal peptide of the pro-protease. Furthermore, an antileukoprotease which specifically inhibits SCCE activity has been recently identified (Wiedow, O. (1995) *Isolierung und Charakterisierung von Serinprotease Inhibitoren der menschlichen Epidermis*, Köster, Berlin). The presence of such an inhibitor might effectively inhibit shedding or desquamation of tumor cells as it has been shown to inhibit the detachment of corneocytes of keratinized skin tissue.

While there remains an intricate interaction between surface protease expression/activation and/or inhibition, it appears likely that a concert of enzymes which contribute to tumor growth and spread provide a mechanism for such a progression. SCCE expression on ovarian tumor cell surfaces can provide one mechanism by which tumor cells may be shed early in the tumor progression process of serous carcinomas.

The unique presence of this protease to keratinized stratum corneum and the present data showing lack of transcript presence in all normal adult and fetal tissues examined support the potential of this secreted extracellular enzyme as a useful marker for ovarian carcinoma. The fact that inhibition of such an activity prevents normal desquamation of skin cells also points to the potential of SCCE as a target for inhibition or down regulation in therapeutic intervention in the spread or metastasis of ovarian carcinoma.

EXAMPLE 17

SCCE Peptides as Target Epitopes for Human $CD8^+$ Cytotoxic T Cells

Two computer programs were used to identify 9-mer peptides containing binding motifs for HLA class I molecules. The first, based on a scheme devised by Parker et al (1994), was developed by the Bioinformatics and Molecular Analysis Section (BIMAS) of the Center for Information Technology, NIH, and the second, known as SYFPEITHI, was formulated by Rammensee and colleagues at the University of Tubingen, Germany.

Peptides that possessed HLA A2.1 binding motifs were synthesized and tested directly for their ability to bind HLA A2.1. This technique employs T2 cells which are peptide transporter-deficient and thus express low endogenous HLA class I levels due to inability to load peptide and stabilize HLA class I folding for surface expression. It has been showed that addition of exogenous peptides capable of binding HLA A2.1 (A*0201) could increase the number of properly folded HLA A2.1 molecules on the cell surface, as revealed by flow cytometry (Nijman et al, 1993).

Monocyte-derived DC were generated from peripheral blood drawn from normal adult donors of the appropriate HLA type. Adherent monocytes were cultured in AIM-V (Gibco-BRL) supplemented with GM-CSF and IL-4 according to standard techniques (Santin et al, 2000). After 5-6 days, DC maturation was induced by addition of $PGE_2$, IL-1b and TNFa for a further 48 h.

Mature DC were loaded with peptide ($2 \times 10^6$ DC with 50 mg/ml peptide in 1 ml serum-free AIM-V medium for 2 h at 37° C.) and washed once prior to culture with $1 \times 10^6$/ml peripheral blood mononuclear cells (PBMC) in AIM-V or AIM-V plus 5% human AB serum. The PBMC:DC ratio was between 20:1 and 30:1. After 7 days, responder T cells were restimulated with peptide-loaded, irradiated autologous DC or PBMC at responder:stimulator ratios between 10:1 and 20:1 or 1:1 and 1:10 respectively. At this point, cultures were supplemented with recombinant human IL-2 (10-100 U/ml), and fed with 50-75% changes of fresh medium plus IL-2 every 24 days. T cell lines were established and maintained by peptide restimulation every 14-21 days. Responder $CD8^+$ T cells were purified by positive selection with anti-CD8-coupled magnetic beads (Dynal, Inc.) after the $2^{nd}$ or $3^{rd}$ antigen stimulation.

Peptide-specific cytotoxicity was tested in standard 5-6 h microwell $^{51}$Cr-release assays (Nazaruk et al, 1998). Autologous EBV-transformed lymphoblastoid cell lines (LCL) were loaded with peptide (50 mg/ml, 1 h at 37° C.) and subsequently $^{51}$Cr-labeled (50 mCi in 200-300 ml, 1 h at 37° C.). Peptide-loaded $^{51}$Cr-labeled LCL were incubated with $CD8^+$ T cells at effector-target ration between 5:1 and 1.25:1. Cytotoxicity was recorded as percentage $^{51}$Cr released into culture supernatants.

SCCE Peptide 5-13

Figure 20:
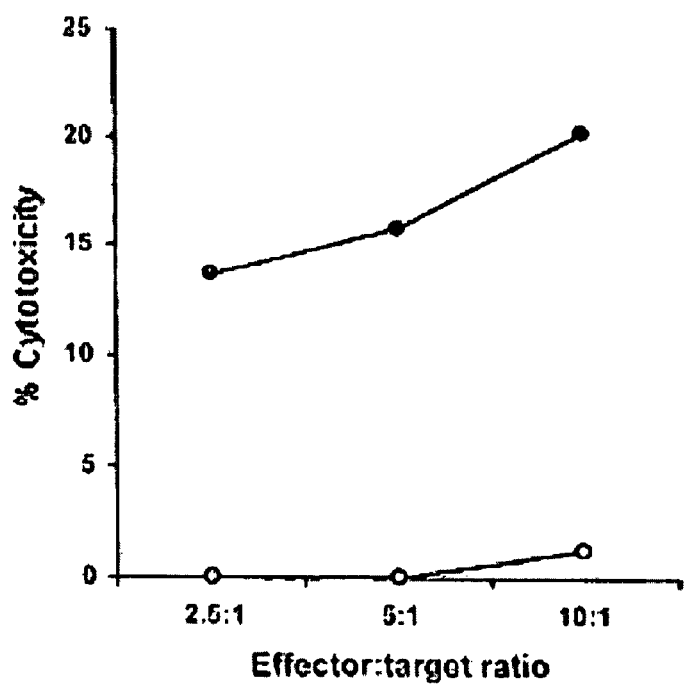
FIG. 20 shows CD8+ CTL recognition of SCCE 5-13 peptide in a 5 hr $^{51}$Cr release assay. Targets were LCL loaded with SCCE 5-13 (●) and control LCL (○).

SCCE peptide 5-13 (SEQ ID NO: 33) is an HLA A2.1-binding peptide, as revealed by upregulation of A2.1 expression in T2 cells (data not shown). $CD8^+$ CTL specific for SCCE 5-13 killed peptide-loaded autologous LCL, but did not kill control, peptide-free LCL. Heterologous HLA A2.1-expressing peptide-loaded LCL were efficiently killed, but targets lacking HLA A2.1 weren't killed (FIG. 20).

SCCE Peptide 123-131

Figure 21:
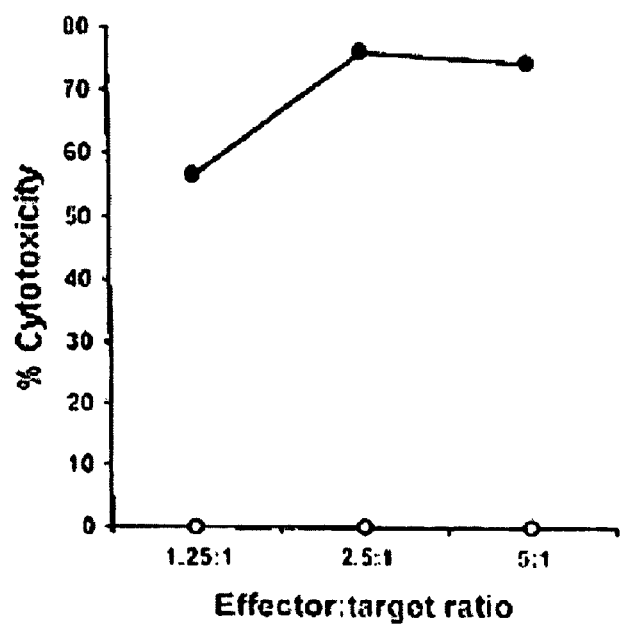
FIG. 21 shows CD8+ CTL recognition of SCCE 123-131 peptide in a 5 hr $^{51}$Cr release assay. Targets were LCL loaded with SCCE 123-131 (●) and control LCL (○).

SCCE peptide 123-131 (SEQ ID NO: 32) is also an HLA A2.1-binding peptide, as revealed by upregulation of A2.1 expression in T2 cells (data not shown). $CD8^+$ CTL specific for SCCE 123-131 killed peptide-loaded autologous LCL, but did not kill control, peptide-free LCL. Heterologous HLA A2.1-expressing peptide-loaded LCL were efficiently killed, but targets lacking HLA A2.1 were not killed (FIG. 21). Natural killer-sensitive K562 cells were not lysed. Cytotoxicity against SCCE 123-131 loaded LCL could be blocked with MAb specific for a non-polymorphic HLA class I determinant, confirming that lysis was HLA class I-restricted.

EXAMPLE 18

Figure 22:
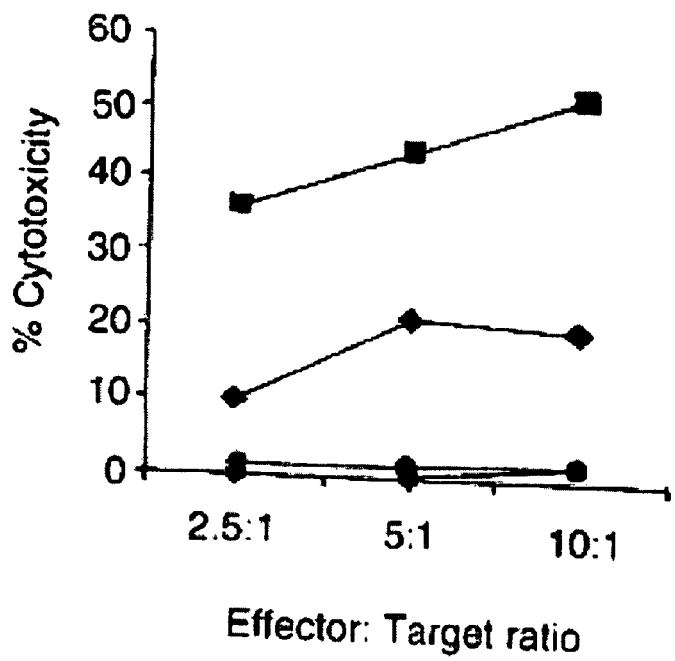
FIG. 22 shows peptide-specific CD8+ CTL recognition of endogenously processed and presented SCCE tumor antigen. CTL were derived by stimulation with dendritic cells pulsed with SCCE peptide 123-131. Cytotoxicity was tested in a standard 5 hours $^{51}$Cr-release assay against autologous macrophages infected with Ad-GFP/SCCE (♦), macrophages infected with Ad-GFP-hepsin (▲), macrophages pulsed with SCCE 123-131 peptide (■), or control untreated macrophages (●).

$CD8^+$ CTL Specific for SCCE Peptide 123-131 Recognize Endogenously Expressed SCCE Tumor Antigen To determine whether peptide-specific $CD8^+$ CTL are capable of recognizing targets that process and present endogenously expressed SCCE tumor antigens, recombinant adenoviruses expressing hepsin and SCCE, both in conjunction with green fluorescent protein (GFP) as a means of directly monitoring expression levels by flow cytometric techniques were constructed. It was found that $CD8^+$ CTL specific for SCCE 123-131 recognize and kill autologous targets infected with recombinant adenoviruses expressing the full-length SCCE antigen (Ad-GFP/SCCE) but did not recognize targets infected with Ad-GFP/hepsin (FIG. 22). These results show that the SCCE 123-131 peptide is a naturally processed and presented CTL epitope for SCCE-specific $CD8^+$ CTL.

Figure 23:
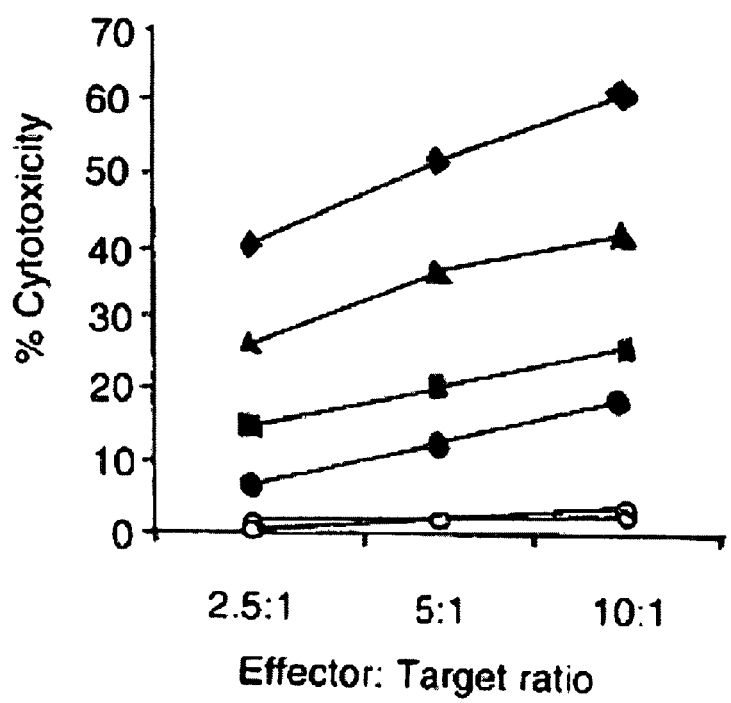
FIG. 23 shows CD8+ CTL specific for SCCE 123-131 lyse ovarian tumor cells. Target cells are autologous LCL loaded with 5 mg/ml peptide (♦), control LCL (open diamond), CaOV-3 ovarian tumor cells (▲), CaOV-3 tumor cells plus ⅕₂₅ dilution of BB7.2 ascites (■), CaOV-3 ovarian tumor cells plus 50 mg/ml W6/32(●), and K562 cells (○).

$CD8^+$ CTL specific for SCCE 123-131 were tested for their ability to lyse HLA-A*0201-matched, SCCE-expressing CaOV-3 ovarian tumor cells. Peptide-specific CTL efficiently lysed peptide-pulsed LCL. The CTL also lysed CaOV-3 tumor cells (FIG. 23). Thus, SCCE 123-131 is a CTL epitope that is processed and presented by ovarian tumor cells. Tumor cell lysis was partially blocked by addition of mAb specific for HLA class I (W6/32) and HLA-A*0201 (BB7.2), indicating that tumor lysis was HLA class I and HLA-A*0201-restricted. Control, unpulsed LCL and NK-sensitive K562 cells were not lysed. These results indicate that ovarian tumor recognition and lysis was an antigen-specific event.

The following references were cited herein:

Egelrud, *J Invest Dermatol* 101:200-204 (1993).
Hall et al., *Mol. Cell. Biol.*, 3: 854-862 (1983).
Hansson et al., *J. Biol. Chem.*, 269:19420-19426 (1994).
Nazaruk et al., *Blood* 91:3875-3883 (1998).
Nijman et al., *Eur. J. Immunol.* 23:1215-1219 (1993).
Noonan et al., *Proc. Natl. Acad. Sci. USA*, 87:7160-7164 (1990).
Parker et al., *J. Immunol.* 152:163-175 (1994).
Powell et al., *Cancer Research*, 53:417-422 (1993).
Sakanari et al., *Biochemistry* 86:4863-4867 (1989).
Santin et al., *Obstetrics & Gynecology* 96:422-430 (2000).
Santin et al., *Am. J. Obstet. Gynecol.* 183:601-609 (2000).
Shigemasa et al., *J Soc Gynecol Invest* 4:95-102, (1997).
Sondell et al., *J Histochem Cytochem* 42:459-465 (1994).
Torres-Rosedo et al., *Proc. Natl. Acad. Sci. USA.* 90:7181-7185 (1993).

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

What is claimed is:

1. An immunogenic composition, comprising an immunogenic fragment of a stratum corneum chymotryptic enzyme protein and an adjuvant, wherein said immunogenic fragment of a stratum corneum enzyme protein is a peptide consisting of the sequence selected from the group consisting of SEQ ID Nos. 31, 32, 33, 34, 35, 36, 80, 86 and 99.

* * * * *

SEQUENCE LISTING

<160> NUMBER OF SEQ ID NOS: 142

<210> SEQ ID NO 1
<211> LENGTH: 23
<212> TYPE: DNA
<213> ORGANISM: Artificial sequence
<220> FEATURE:

```
<221> NAME/KEY: primer_bind
<222> LOCATION: 6, 9, 12, 15, 18
<223> OTHER INFORMATION: sense oligonucleotide primer for amplifying
      serine proteases, n = Inosine

<400> SEQUENCE: 1
tgggtngtna cngcngcnca ytg                                          23

<210> SEQ ID NO 2
<211> LENGTH: 20
<212> TYPE: DNA
<213> ORGANISM: Artificial sequence
<220> FEATURE:
<221> NAME/KEY: primer_bind
<222> LOCATION: 3, 6, 9, 12, 15, 18
<223> OTHER INFORMATION: antisense oligonucleotide primer for amplifying
      serine proteases, n = Inosine

<400> SEQUENCE: 2
arnarngcna tntcnttncc                                              20

<210> SEQ ID NO 3
<211> LENGTH: 20
<212> TYPE: DNA
<213> ORGANISM: Artificial sequence
<220> FEATURE:
<221> NAME/KEY: primer_bind
<222> LOCATION: 3, 6, 9, 12, 18
<223> OTHER INFORMATION: antisense oligonucleotide primer for amplifying
      serine proteases, n = Inosine

<400> SEQUENCE: 3
arnggnccnc cnswrtcncc                                              20

<210> SEQ ID NO 4
<211> LENGTH: 24
<212> TYPE: DNA
<213> ORGANISM: Artificial sequence
<220> FEATURE:
<221> NAME/KEY: primer_bind
<222> LOCATION: 6, 15, 18
<223> OTHER INFORMATION: sense oligonucleotide primer for amplifying
      cysteine proteases, n = Inosine

<400> SEQUENCE: 4
carggncart gyggnwsntg ytgg                                         24

<210> SEQ ID NO 5
<211> LENGTH: 20
<212> TYPE: DNA
<213> ORGANISM: Artificial sequence
<220> FEATURE:
<221> NAME/KEY: primer_bind
<222> LOCATION: 3, 6, 15
<223> OTHER INFORMATION: antisense oligonucleotide primer for amplifying
      cysteine proteases, n = Inosine

<400> SEQUENCE: 5
tanccnccrt trcanccytc                                              20

<210> SEQ ID NO 6
<211> LENGTH: 20
<212> TYPE: DNA
<213> ORGANISM: Artificial sequence
<220> FEATURE:
<221> NAME/KEY: primer_bind
<222> LOCATION: 3, 6, 12, 15, 18
<223> OTHER INFORMATION: sense oligonucleotide primer for amplifying
      metallo-proteases, n = Inosine
```

```
<400> SEQUENCE: 6
ccnmgntgyg gnrwnccnga                                          20

<210> SEQ ID NO 7
<211> LENGTH: 17
<212> TYPE: DNA
<213> ORGANISM: Artificial sequence
<220> FEATURE:
<221> NAME/KEY: primer_bind
<222> LOCATION: 6, 9, 11
<223> OTHER INFORMATION: antisense oligonucleotide primer for amplifying
      metallo-proteases, n = Inosine

<400> SEQUENCE: 7
ttrtgnccna nytcrtg                                             17

<210> SEQ ID NO 8
<211> LENGTH: 20
<212> TYPE: DNA
<213> ORGANISM: Artificial sequence
<220> FEATURE:
<221> NAME/KEY: primer_bind
<223> OTHER INFORMATION: sense oligonucleotide primer specific for
      hepsin

<400> SEQUENCE: 8
tgtcccgatg gcgagtgttt                                          20

<210> SEQ ID NO 9
<211> LENGTH: 20
<212> TYPE: DNA
<213> ORGANISM: Artificial sequence
<220> FEATURE:
<221> NAME/KEY: primer_bind
<223> OTHER INFORMATION: antisense oligonucleotide primer specific for
      hepsin

<400> SEQUENCE: 9
cctgttggcc atagtactgc                                          20

<210> SEQ ID NO 10
<211> LENGTH: 20
<212> TYPE: DNA
<213> ORGANISM: Artificial sequence
<220> FEATURE:
<221> NAME/KEY: primer_bind
<223> OTHER INFORMATION: sense oligonucleotide primer specific for SCCE

<400> SEQUENCE: 10
agatgaatga gtacaccgtg                                          20

<210> SEQ ID NO 11
<211> LENGTH: 20
<212> TYPE: DNA
<213> ORGANISM: Artificial sequence
<220> FEATURE:
<221> NAME/KEY: primer_bind
<223> OTHER INFORMATION: antisense oligonucleotide primer specific for
      SCCE

<400> SEQUENCE: 11
ccagtaagtc cttgtaaacc                                          20

<210> SEQ ID NO 12
<211> LENGTH: 20
<212> TYPE: DNA
<213> ORGANISM: Artificial sequence
<220> FEATURE:
```

```
<221> NAME/KEY: primer_bind
<223> OTHER INFORMATION: sense oligonucleotide primer specific for CompB

<400> SEQUENCE: 12
aagggacacg agagctgtat                                               20

<210> SEQ ID NO 13
<211> LENGTH: 20
<212> TYPE: DNA
<213> ORGANISM: Artificial sequence
<220> FEATURE:
<221> NAME/KEY: primer_bind
<223> OTHER INFORMATION: antisense oligonucleotide primer specific for
      CompB

<400> SEQUENCE: 13
aagtggtagt tggaggaagc                                               20

<210> SEQ ID NO 14
<211> LENGTH: 20
<212> TYPE: DNA
<213> ORGANISM: Artificial sequence
<220> FEATURE:
<221> NAME/KEY: primer_bind
<223> OTHER INFORMATION: sense oligonucleotide primer specific for
      Cath-L

<400> SEQUENCE: 14
attggagaga gaaaggctac                                               20

<210> SEQ ID NO 15
<211> LENGTH: 20
<212> TYPE: DNA
<213> ORGANISM: Artificial sequence
<220> FEATURE:
<221> NAME/KEY: primer_bind
<223> OTHER INFORMATION: antisense oligonucleotide primer specific for
      Cath-L

<400> SEQUENCE: 15
cttgggattg tacttacagg                                               20

<210> SEQ ID NO 16
<211> LENGTH: 20
<212> TYPE: DNA
<213> ORGANISM: Artificial sequence
<220> FEATURE:
<221> NAME/KEY: primer_bind
<223> OTHER INFORMATION: sense oligonucleotide primer specific for
      PUMP-1

<400> SEQUENCE: 16
cttccaaagt ggtcacctac                                               20

<210> SEQ ID NO 17
<211> LENGTH: 20
<212> TYPE: DNA
<213> ORGANISM: Artificial sequence
<220> FEATURE:
<221> NAME/KEY: primer_bind
<223> OTHER INFORMATION: antisense oligonucleotide primer specific for
      PUMP-1

<400> SEQUENCE: 17
ctagactgct accatccgtc                                               20

<210> SEQ ID NO 18
<211> LENGTH: 17
```

```
<212> TYPE: DNA
<213> ORGANISM: Artificial sequence
<220> FEATURE:
<221> NAME/KEY: primer_bind
<223> OTHER INFORMATION: sense oligonucleotide primer specific for
      beta-tubulin

<400> SEQUENCE: 18
tgcattgaca acgaggc                                                        17

<210> SEQ ID NO 19
<211> LENGTH: 17
<212> TYPE: DNA
<213> ORGANISM: Artificial sequence
<220> FEATURE:
<221> NAME/KEY: primer_bind
<223> OTHER INFORMATION: antisense oligonucleotide primer specific for
      beta-tubulin

<400> SEQUENCE: 19
ctgtcttgac attgttg                                                        17

<210> SEQ ID NO 20
<211> LENGTH: 20
<212> TYPE: DNA
<213> ORGANISM: Artificial sequence
<220> FEATURE:
<221> NAME/KEY: primer_bind
<223> OTHER INFORMATION: sense oligonucleotide primer specific for
      Protease M

<400> SEQUENCE: 20
ctgtgatcca ccctgactat                                                     20

<210> SEQ ID NO 21
<211> LENGTH: 20
<212> TYPE: DNA
<213> ORGANISM: Artificial sequence
<220> FEATURE:
<221> NAME/KEY: primer_bind
<223> OTHER INFORMATION: antisense oligonucleotide primer specific for
      Protease M

<400> SEQUENCE: 21
caggtggatg tatgcacact                                                     20

<210> SEQ ID NO 22
<211> LENGTH: 20
<212> TYPE: DNA
<213> ORGANISM: Artificial sequence
<220> FEATURE:
<221> NAME/KEY: primer_bind
<223> OTHER INFORMATION: sense oligonucleotide primer specific for
      TADG-12

<400> SEQUENCE: 22
gcgcactgtg tttatgagat                                                     20

<210> SEQ ID NO 23
<211> LENGTH: 20
<212> TYPE: DNA
<213> ORGANISM: Artificial sequence
<220> FEATURE:
<221> NAME/KEY: primer_bind
<223> OTHER INFORMATION: antisense oligonucleotide primer specific for
      TADG-12

<400> SEQUENCE: 23
ctctttggct tgtacttgct                                                     20
```

```
<210> SEQ ID NO 24
<211> LENGTH: 20
<212> TYPE: DNA
<213> ORGANISM: Artificial sequence
<220> FEATURE:
<221> NAME/KEY: primer_bind
<223> OTHER INFORMATION: sense oligonucleotide primer specific for
      TADG-13

<400> SEQUENCE: 24
tgagggacat cattatgcac                                                   20

<210> SEQ ID NO 25
<211> LENGTH: 20
<212> TYPE: DNA
<213> ORGANISM: Artificial sequence
<220> FEATURE:
<221> NAME/KEY: primer_bind
<223> OTHER INFORMATION: antisense oligonucleotide primer specific for
      TADG-13

<400> SEQUENCE: 25 caagtttcc ccataattgg                                                    20

<210> SEQ ID NO 26
<211> LENGTH: 20
<212> TYPE: DNA
<213> ORGANISM: Artificial sequence
<220> FEATURE:
<221> NAME/KEY: primer_bind
<223> OTHER INFORMATION: sense oligonucleotide primer specific for
      TADG-14

<400> SEQUENCE: 26
acagtacgcc tgggagacca                                                   20

<210> SEQ ID NO 27
<211> LENGTH: 20
<212> TYPE: DNA
<213> ORGANISM: Artificial sequence
<220> FEATURE:
<221> NAME/KEY: primer_bind
<223> OTHER INFORMATION: antisense oligonucleotide primer specific for
      TADG-14

<400> SEQUENCE: 27
ctgagacggt gcaattctgg                                                   20

<210> SEQ ID NO 28
<211> LENGTH: 12
<212> TYPE: PRT
<213> ORGANISM: Unknown
<220> FEATURE:
<221> NAME/KEY: CHAIN
<223> OTHER INFORMATION: a poly-lysine linked multiple Ag peptide
      derived from SCCE protein sequences

<400> SEQUENCE: 28

Pro Leu Gln Ile Leu Leu Leu Ser Leu Ala Leu Glu
                5                   10

<210> SEQ ID NO 29
<211> LENGTH: 12
<212> TYPE: PRT
<213> ORGANISM: Unknown
<220> FEATURE:
<221> NAME/KEY: CHAIN
<223> OTHER INFORMATION: a poly-lysine linked multiple Ag peptide
``` derived from SCCE protein sequences

<400> SEQUENCE: 29

Ser Phe Arg His Pro Gly Tyr Ser Thr Gln Thr His
                5                   10

<210> SEQ ID NO 30
<211> LENGTH: 969
<212> TYPE: DNA
<213> ORGANISM: Homo sapiens
<220> FEATURE:
<221> NAME/KEY: mat_peptide
<223> OTHER INFORMATION: full length cDNA of SCCE

<400> SEQUENCE: 30

| | |
|---|---|
| ggatttccgg gctccatggc aagatccctt ctcctgcccc tgcagatctt | 50 |
| actgctatcc ttagccttgg aaactgcagg agaagaagcc cagggtgaca | 100 |
| agattattga tggcgcccca tgtgcaagag gctcccaccc atggcaggtg | 150 |
| gccctgctca gtggcaatca gctccactgc ggaggcgtcc tggtcaatga | 200 |
| gcgctgggtg ctcactgccg cccactgcaa gatgaatgag tacaccgtgc | 250 |
| acctgggcag tgatacgctg ggcgacagga gagctcagag gatcaaggcc | 300 |
| tcgaagtcat tccgccaccc cggctactcc acacagaccc atgttaatga | 350 |
| cctcatgctc gtgaagctca atagccaggc caggctgtca tccatggtga | 400 |
| agaaagtcag gctgccctcc cgctgcgaac cccctggaac cacctgtact | 450 |
| gtctccggct ggggcactac cacgagccca gatgtgacct ttccctctga | 500 |
| cctcatgtgc gtggatgtca agctcatctc ccccaggac tgcacgaagg | 550 |
| tttacaagga cttactggaa aattccatgc tgtgcgctgg catccccgac | 600 |
| tccaagaaaa acgcctgcaa tggtgactca ggggaccgt tggtgtgcag | 650 |
| aggtaccctg caaggtctgg tgtcctgggg aactttccct tgcggccaac | 700 |
| ccaatgaccc aggagtctac actcaagtgt gcaagttcac caagtggata | 750 |
| aatgacacca tgaaaagca tcgctaacgc cacactgagt taattaactg | 800 |
| tgtgcttcca acagaaaatg cacaggagtg aggacgccga tgacctatga | 850 |
| agtcaaattt gactttacct ttcctcaaag atatatttaa acctcatgcc | 900 |
| ctgttgataa accaatcaaa ttggtaaaga cctaaaacca aaacaaataa | 950 |
| agaaacacaa aaccctcag | 969 |

<210> SEQ ID NO 31
<211> LENGTH: 9
<212> TYPE: PRT
<213> ORGANISM: Homo sapiens
<220> FEATURE:
<221> NAME/KEY: CHAIN
<223> OTHER INFORMATION: Residues 72-80 of the SCCE protein

<400> SEQUENCE: 31

Lys Met Asn Glu Tyr Thr Val His Leu
                5

<210> SEQ ID NO 32
<211> LENGTH: 9
<212> TYPE: PRT
<213> ORGANISM: Homo sapiens
<220> FEATURE:
<221> NAME/KEY: CHAIN
<223> OTHER INFORMATION: Residues 123-131 of the SCCE protein

```
<400> SEQUENCE: 32

Arg Leu Ser Ser Met Val Lys Lys Val
                5

<210> SEQ ID NO 33
<211> LENGTH: 9
<212> TYPE: PRT
<213> ORGANISM: Homo sapiens
<220> FEATURE:
<221> NAME/KEY: CHAIN
<223> OTHER INFORMATION: Residues 5-13 of the SCCE protein

<400> SEQUENCE: 33

Leu Leu Leu Pro Leu Gln Ile Leu Leu
                5

<210> SEQ ID NO 34
<211> LENGTH: 9
<212> TYPE: PRT
<213> ORGANISM: Homo sapiens
<220> FEATURE:
<221> NAME/KEY: CHAIN
<223> OTHER INFORMATION: Residues 58-66 of the SCCE protein

<400> SEQUENCE: 34

Val Leu Val Asn Glu Arg Trp Val Leu
                5

<210> SEQ ID NO 35
<211> LENGTH: 9
<212> TYPE: PRT
<213> ORGANISM: Homo sapiens
<220> FEATURE:
<221> NAME/KEY: CHAIN
<223> OTHER INFORMATION: Residues 6-14 of the SCCE protein

<400> SEQUENCE: 35

Leu Leu Pro Leu Gln Ile Leu Leu Leu
                5

<210> SEQ ID NO 36
<211> LENGTH: 9
<212> TYPE: PRT
<213> ORGANISM: Homo sapiens
<220> FEATURE:
<221> NAME/KEY: CHAIN
<223> OTHER INFORMATION: Residues 4-12 of the SCCE protein

<400> SEQUENCE: 36

Ser Leu Leu Leu Pro Leu Gln Ile Leu
                5

<210> SEQ ID NO 37
<211> LENGTH: 9
<212> TYPE: PRT
<213> ORGANISM: Homo sapiens
<220> FEATURE:
<221> NAME/KEY: CHAIN
<223> OTHER INFORMATION: Residues 52-60 of the SCCE protein

<400> SEQUENCE: 37

Gln Leu His Cys Gly Gly Val Leu Val
                5

<210> SEQ ID NO 38
<211> LENGTH: 9
<212> TYPE: PRT
```

```
<213> ORGANISM: Homo sapiens
<220> FEATURE:
<221> NAME/KEY: CHAIN
<223> OTHER INFORMATION: Residues 12-20 of the SCCE protein

<400> SEQUENCE: 38

Leu Leu Leu Ser Leu Ala Leu Glu Thr
              5

<210> SEQ ID NO 39
<211> LENGTH: 9
<212> TYPE: PRT
<213> ORGANISM: Homo sapiens
<220> FEATURE:
<221> NAME/KEY: CHAIN
<223> OTHER INFORMATION: Residues 163-171 of the SCCE protein

<400> SEQUENCE: 39

Leu Met Cys Val Asp Val Lys Leu Ile
              5

<210> SEQ ID NO 40
<211> LENGTH: 9
<212> TYPE: PRT
<213> ORGANISM: Homo sapiens
<220> FEATURE:
<221> NAME/KEY: CHAIN
<223> OTHER INFORMATION: Residues 57-65 of the SCCE protein

<400> SEQUENCE: 40

Gly Val Leu Val Asn Glu Arg Trp Val
              5

<210> SEQ ID NO 41
<211> LENGTH: 9
<212> TYPE: PRT
<213> ORGANISM: Homo sapiens
<220> FEATURE:
<221> NAME/KEY: CHAIN
<223> OTHER INFORMATION: Residues 237-245 of the SCCE protein

<400> SEQUENCE: 41

Gln Val Cys Lys Phe Thr Lys Trp Ile
              5

<210> SEQ ID NO 42
<211> LENGTH: 9
<212> TYPE: PRT
<213> ORGANISM: Homo sapiens
<220> FEATURE:
<221> NAME/KEY: CHAIN
<223> OTHER INFORMATION: Residues 169-177 of the SCCE protein

<400> SEQUENCE: 42

Lys Leu Ile Ser Pro Gln Asp Cys Thr
              5

<210> SEQ ID NO 43
<211> LENGTH: 9
<212> TYPE: PRT
<213> ORGANISM: Homo sapiens
<220> FEATURE:
<221> NAME/KEY: CHAIN
<223> OTHER INFORMATION: Residues 10-18 of the SCCE protein

<400> SEQUENCE: 43

Gln Ile Leu Leu Leu Ser Leu Ala Leu
              5
```

-continued

```
<210> SEQ ID NO 44
<211> LENGTH: 9
<212> TYPE: PRT
<213> ORGANISM: Homo sapiens
<220> FEATURE:
<221> NAME/KEY: CHAIN
<223> OTHER INFORMATION: Residues 29-37 of the SCCE protein

<400> SEQUENCE: 44

Lys Ile Ile Asp Gly Ala Pro Cys Ala
                5

<210> SEQ ID NO 45
<211> LENGTH: 9
<212> TYPE: PRT
<213> ORGANISM: Homo sapiens
<220> FEATURE:
<221> NAME/KEY: CHAIN
<223> OTHER INFORMATION: Residues 215-223 of the SCCE protein

<400> SEQUENCE: 45

Leu Gln Gly Leu Val Ser Trp Gly Thr
                5

<210> SEQ ID NO 46
<211> LENGTH: 9
<212> TYPE: PRT
<213> ORGANISM: Homo sapiens
<220> FEATURE:
<221> NAME/KEY: CHAIN
<223> OTHER INFORMATION: Residues 13-21 of the SCCE protein

<400> SEQUENCE: 46

Leu Leu Ser Leu Ala Leu Glu Thr Ala
                5

<210> SEQ ID NO 47
<211> LENGTH: 9
<212> TYPE: PRT
<213> ORGANISM: Homo sapiens
<220> FEATURE:
<221> NAME/KEY: CHAIN
<223> OTHER INFORMATION: Residues 114-122 of the SCCE protein

<400> SEQUENCE: 47

Met Leu Val Lys Leu Asn Ser Gln Ala
                5

<210> SEQ ID NO 48
<211> LENGTH: 9
<212> TYPE: PRT
<213> ORGANISM: Homo sapiens
<220> FEATURE:
<221> NAME/KEY: CHAIN
<223> OTHER INFORMATION: Residues 47-55 of the SCCE protein

<400> SEQUENCE: 48

Leu Leu Ser Gly Asn Gln Leu His Cys
                5

<210> SEQ ID NO 49
<211> LENGTH: 9
<212> TYPE: PRT
<213> ORGANISM: Homo sapiens
<220> FEATURE:
<221> NAME/KEY: CHAIN
<223> OTHER INFORMATION: Residues 65-73 of the SCCE protein

<400> SEQUENCE: 49
```

Val Leu Thr Ala Ala His Cys Lys Met
            5

<210> SEQ ID NO 50
<211> LENGTH: 9
<212> TYPE: PRT
<213> ORGANISM: Homo sapiens
<220> FEATURE:
<221> NAME/KEY: CHAIN
<223> OTHER INFORMATION: Residues 59-67 of the SCCE protein

<400> SEQUENCE: 50

Leu Val Asn Glu Arg Trp Val Leu Thr
            5

<210> SEQ ID NO 51
<211> LENGTH: 9
<212> TYPE: PRT
<213> ORGANISM: Homo sapiens
<220> FEATURE:
<221> NAME/KEY: CHAIN
<223> OTHER INFORMATION: Residues 51-59 of the SCCE protein

<400> SEQUENCE: 51

Asn Gln Leu His Cys Gly Gly Val Leu
            5

<210> SEQ ID NO 52
<211> LENGTH: 9
<212> TYPE: PRT
<213> ORGANISM: Homo sapiens
<220> FEATURE:
<221> NAME/KEY: CHAIN
<223> OTHER INFORMATION: Residues 77-85 of the SCCE protein

<400> SEQUENCE: 52

Thr Val His Leu Gly Ser Asp Thr Leu
            5

<210> SEQ ID NO 53
<211> LENGTH: 9
<212> TYPE: PRT
<213> ORGANISM: Homo sapiens
<220> FEATURE:
<221> NAME/KEY: CHAIN
<223> OTHER INFORMATION: Residues 45-53 of the SCCE protein

<400> SEQUENCE: 53

Val Ala Leu Leu Ser Gly Asn Gln Leu
            5

<210> SEQ ID NO 54
<211> LENGTH: 9
<212> TYPE: PRT
<213> ORGANISM: Homo sapiens
<220> FEATURE:
<221> NAME/KEY: CHAIN
<223> OTHER INFORMATION: Residues 162-170 of the SCCE protein

<400> SEQUENCE: 54

Asp Leu Met Cys Val Asp Val Lys Leu
            5

<210> SEQ ID NO 55
<211> LENGTH: 9
<212> TYPE: PRT
<213> ORGANISM: Homo sapiens
<220> FEATURE:

```
<221> NAME/KEY: CHAIN
<223> OTHER INFORMATION: Residues 218-226 of the SCCE protein

<400> SEQUENCE: 55

Leu Val Ser Trp Gly Thr Phe Pro Cys
                5

<210> SEQ ID NO 56
<211> LENGTH: 9
<212> TYPE: PRT
<213> ORGANISM: Homo sapiens
<220> FEATURE:
<221> NAME/KEY: CHAIN
<223> OTHER INFORMATION: Residues 145-153 of the SCCE protein

<400> SEQUENCE: 56

Thr Val Ser Gly Trp Gly Thr Thr Thr
                5

<210> SEQ ID NO 57
<211> LENGTH: 9
<212> TYPE: PRT
<213> ORGANISM: Homo sapiens
<220> FEATURE:
<221> NAME/KEY: CHAIN
<223> OTHER INFORMATION: Residues 136-144 of the SCCE protein

<400> SEQUENCE: 57

Arg Cys Glu Pro Pro Gly Thr Thr Cys
                5

<210> SEQ ID NO 58
<211> LENGTH: 9
<212> TYPE: PRT
<213> ORGANISM: Homo sapiens
<220> FEATURE:
<221> NAME/KEY: CHAIN
<223> OTHER INFORMATION: Residues 81-89 of the SCCE protein

<400> SEQUENCE: 58

Gly Ser Asp Thr Leu Gly Asp Arg Arg
                5

<210> SEQ ID NO 59
<211> LENGTH: 9
<212> TYPE: PRT
<213> ORGANISM: Homo sapiens
<220> FEATURE:
<221> NAME/KEY: CHAIN
<223> OTHER INFORMATION: Residues 30-38 of the SCCE protein

<400> SEQUENCE: 59

Ile Ile Asp Gly Ala Pro Cys Ala Arg
                5

<210> SEQ ID NO 60
<211> LENGTH: 9
<212> TYPE: PRT
<213> ORGANISM: Homo sapiens
<220> FEATURE:
<221> NAME/KEY: CHAIN
<223> OTHER INFORMATION: Residues 183-191 of the SCCE protein

<400> SEQUENCE: 60

Leu Leu Glu Asn Ser Met Leu Cys Ala
                5

<210> SEQ ID NO 61
```

```
<211> LENGTH: 9
<212> TYPE: PRT
<213> ORGANISM: Homo sapiens
<220> FEATURE:
<221> NAME/KEY: CHAIN
<223> OTHER INFORMATION: Residues 21-29 of the SCCE protein

<400> SEQUENCE: 61

Ala Gly Glu Glu Ala Gln Gly Asp Lys
                5

<210> SEQ ID NO 62
<211> LENGTH: 9
<212> TYPE: PRT
<213> ORGANISM: Homo sapiens
<220> FEATURE:
<221> NAME/KEY: CHAIN
<223> OTHER INFORMATION: Residues 235-243 of the SCCE protein

<400> SEQUENCE: 62

Tyr Thr Gln Val Cys Lys Phe Thr Lys
                5

<210> SEQ ID NO 63
<211> LENGTH: 9
<212> TYPE: PRT
<213> ORGANISM: Homo sapiens
<220> FEATURE:
<221> NAME/KEY: CHAIN
<223> OTHER INFORMATION: Residues 170-178 of the SCCE protein

<400> SEQUENCE: 63

Leu Ile Ser Pro Gln Asp Cys Thr Lys
                5

<210> SEQ ID NO 64
<211> LENGTH: 9
<212> TYPE: PRT
<213> ORGANISM: Homo sapiens
<220> FEATURE:
<221> NAME/KEY: CHAIN
<223> OTHER INFORMATION: Residues 245-253 of the SCCE protein

<400> SEQUENCE: 64

Ile Asn Asp Thr Met Lys Lys His Arg
                5

<210> SEQ ID NO 65
<211> LENGTH: 9
<212> TYPE: PRT
<213> ORGANISM: Homo sapiens
<220> FEATURE:
<221> NAME/KEY: CHAIN
<223> OTHER INFORMATION: Residues 157-165 of the SCCE protein

<400> SEQUENCE: 65

Val Thr Phe Pro Ser Asp Leu Met Cys
                5

<210> SEQ ID NO 66
<211> LENGTH: 9
<212> TYPE: PRT
<213> ORGANISM: Homo sapiens
<220> FEATURE:
<221> NAME/KEY: CHAIN
<223> OTHER INFORMATION: Residues 109-117 of the SCCE protein

<400> SEQUENCE: 66

His Val Asn Asp Leu Met Leu Val Lys
```

```
<210> SEQ ID NO 67
<211> LENGTH: 9
<212> TYPE: PRT
<213> ORGANISM: Homo sapiens
<220> FEATURE:
<221> NAME/KEY: CHAIN
<223> OTHER INFORMATION: Residues 17-25 of the SCCE protein

<400> SEQUENCE: 67

Ala Leu Glu Thr Ala Gly Glu Glu Ala
                5

<210> SEQ ID NO 68
<211> LENGTH: 9
<212> TYPE: PRT
<213> ORGANISM: Homo sapiens
<220> FEATURE:
<221> NAME/KEY: CHAIN
<223> OTHER INFORMATION: Residues 151-159 of the SCCE protein

<400> SEQUENCE: 68

Thr Thr Thr Ser Pro Asp Val Thr Phe
                5

<210> SEQ ID NO 69
<211> LENGTH: 9
<212> TYPE: PRT
<213> ORGANISM: Homo sapiens
<220> FEATURE:
<221> NAME/KEY: CHAIN
<223> OTHER INFORMATION: Residues 68-76 of the SCCE protein

<400> SEQUENCE: 69

Ala Ala His Cys Lys Met Asn Glu Tyr
                5

<210> SEQ ID NO 70
<211> LENGTH: 9
<212> TYPE: PRT
<213> ORGANISM: Homo sapiens
<220> FEATURE:
<221> NAME/KEY: CHAIN
<223> OTHER INFORMATION: Residues 173-181 of the SCCE protein

<400> SEQUENCE: 70

Pro Gln Asp Cys Thr Lys Val Tyr Lys
                5

<210> SEQ ID NO 71
<211> LENGTH: 9
<212> TYPE: PRT
<213> ORGANISM: Homo sapiens
<220> FEATURE:
<221> NAME/KEY: CHAIN
<223> OTHER INFORMATION: Residues 204-212 of the SCCE protein

<400> SEQUENCE: 71

Asp Ser Gly Gly Pro Leu Val Cys Arg
                5

<210> SEQ ID NO 72
<211> LENGTH: 9
<212> TYPE: PRT
<213> ORGANISM: Homo sapiens
<220> FEATURE:
<221> NAME/KEY: CHAIN
<223> OTHER INFORMATION: Residues 39-47 of the SCCE protein
```

```
<400> SEQUENCE: 72

Gly Ser His Pro Trp Gln Val Ala Leu
                5

<210> SEQ ID NO 73
<211> LENGTH: 9
<212> TYPE: PRT
<213> ORGANISM: Homo sapiens
<220> FEATURE:
<221> NAME/KEY: CHAIN
<223> OTHER INFORMATION: Residues 222-230 of the SCCE protein

<400> SEQUENCE: 73

Gly Thr Phe Pro Cys Gly Gln Pro Asn
                5

<210> SEQ ID NO 74
<211> LENGTH: 9
<212> TYPE: PRT
<213> ORGANISM: Homo sapiens
<220> FEATURE:
<221> NAME/KEY: CHAIN
<223> OTHER INFORMATION: Residues 165-173 of the SCCE protein

<400> SEQUENCE: 74

Cys Val Asp Val Lys Leu Ile Ser Pro
                5

<210> SEQ ID NO 75
<211> LENGTH: 9
<212> TYPE: PRT
<213> ORGANISM: Homo sapiens
<220> FEATURE:
<221> NAME/KEY: CHAIN
<223> OTHER INFORMATION: Residues 110-118 of the SCCE protein

<400> SEQUENCE: 75

Val Asn Asp Leu Met Leu Val Lys Leu
                5

<210> SEQ ID NO 76
<211> LENGTH: 9
<212> TYPE: PRT
<213> ORGANISM: Homo sapiens
<220> FEATURE:
<221> NAME/KEY: CHAIN
<223> OTHER INFORMATION: Residues 179-187 of the SCCE protein

<400> SEQUENCE: 76

Val Tyr Lys Asp Leu Leu Glu Asn Ser
                5

<210> SEQ ID NO 77
<211> LENGTH: 9
<212> TYPE: PRT
<213> ORGANISM: Homo sapiens
<220> FEATURE:
<221> NAME/KEY: CHAIN
<223> OTHER INFORMATION: Residues 105-113 of the SCCE protein

<400> SEQUENCE: 77

Ser Thr Gln Thr His Val Asn Asp Leu
                5

<210> SEQ ID NO 78
<211> LENGTH: 9
<212> TYPE: PRT
```

```
<213> ORGANISM: Homo sapiens
<220> FEATURE:
<221> NAME/KEY: CHAIN
<223> OTHER INFORMATION: Residues 234-242 of the SCCE protein

<400> SEQUENCE: 78

Val Tyr Thr Gln Val Cys Lys Phe Thr
                5

<210> SEQ ID NO 79
<211> LENGTH: 9
<212> TYPE: PRT
<213> ORGANISM: Homo sapiens
<220> FEATURE:
<221> NAME/KEY: CHAIN
<223> OTHER INFORMATION: Residues 125-133 of the SCCE protein

<400> SEQUENCE: 79

Ser Ser Met Val Lys Lys Val Arg Leu
                5

<210> SEQ ID NO 80
<211> LENGTH: 9
<212> TYPE: PRT
<213> ORGANISM: Homo sapiens
<220> FEATURE:
<221> NAME/KEY: CHAIN
<223> OTHER INFORMATION: Residues 207-215 of the SCCE protein

<400> SEQUENCE: 80

Gly Pro Leu Val Cys Arg Gly Thr Leu
                5

<210> SEQ ID NO 81
<211> LENGTH: 9
<212> TYPE: PRT
<213> ORGANISM: Homo sapiens
<220> FEATURE:
<221> NAME/KEY: CHAIN
<223> OTHER INFORMATION: Residues 51-59 of the SCCE protein

<400> SEQUENCE: 81

Asn Gln Leu His Cys Gly Gly Val Leu
                5

<210> SEQ ID NO 82
<211> LENGTH: 9
<212> TYPE: PRT
<213> ORGANISM: Homo sapiens
<220> FEATURE:
<221> NAME/KEY: CHAIN
<223> OTHER INFORMATION: Residues 175-183 of the SCCE protein

<400> SEQUENCE: 82

Asp Cys Thr Lys Val Tyr Lys Asp Leu
                5

<210> SEQ ID NO 83
<211> LENGTH: 9
<212> TYPE: PRT
<213> ORGANISM: Homo sapiens
<220> FEATURE:
<221> NAME/KEY: CHAIN
<223> OTHER INFORMATION: Residues 103-111 of the SCCE protein

<400> SEQUENCE: 83

Gly Tyr Ser Thr Gln Thr His Val Asn
                5
```

```
<210> SEQ ID NO 84
<211> LENGTH: 9
<212> TYPE: PRT
<213> ORGANISM: Homo sapiens
<220> FEATURE:
<221> NAME/KEY: CHAIN
<223> OTHER INFORMATION: Residues 201-209 of the SCCE protein

<400> SEQUENCE: 84

Cys Asn Gly Asp Ser Gly Gly Pro Leu
                5

<210> SEQ ID NO 85
<211> LENGTH: 9
<212> TYPE: PRT
<213> ORGANISM: Homo sapiens
<220> FEATURE:
<221> NAME/KEY: CHAIN
<223> OTHER INFORMATION: Residues 210-218 of the SCCE protein

<400> SEQUENCE: 85

Val Cys Arg Gly Thr Leu Gln Gly Leu
                5

<210> SEQ ID NO 86
<211> LENGTH: 9
<212> TYPE: PRT
<213> ORGANISM: Homo sapiens
<220> FEATURE:
<221> NAME/KEY: CHAIN
<223> OTHER INFORMATION: Residues 1-9 of the SCCE protein

<400> SEQUENCE: 86

Met Ala Arg Ser Leu Leu Leu Pro Leu
                5

<210> SEQ ID NO 87
<211> LENGTH: 9
<212> TYPE: PRT
<213> ORGANISM: Homo sapiens
<220> FEATURE:
<221> NAME/KEY: CHAIN
<223> OTHER INFORMATION: Residues 125-133 of the SCCE protein

<400> SEQUENCE: 87

Ser Ser Met Val Lys Lys Val Arg Leu
                5

<210> SEQ ID NO 88
<211> LENGTH: 9
<212> TYPE: PRT
<213> ORGANISM: Homo sapiens
<220> FEATURE:
<221> NAME/KEY: CHAIN
<223> OTHER INFORMATION: Residues 156-164 of the SCCE protein

<400> SEQUENCE: 88

Asp Val Thr Phe Pro Ser Asp Leu Met
                5

<210> SEQ ID NO 89
<211> LENGTH: 9
<212> TYPE: PRT
<213> ORGANISM: Homo sapiens
<220> FEATURE:
<221> NAME/KEY: CHAIN
<223> OTHER INFORMATION: Residues 72-80 of the SCCE protein

<400> SEQUENCE: 89
```

```
Lys Met Asn Glu Tyr Thr Val His Leu
                5

<210> SEQ ID NO 90
<211> LENGTH: 9
<212> TYPE: PRT
<213> ORGANISM: Homo sapiens
<220> FEATURE:
<221> NAME/KEY: CHAIN
<223> OTHER INFORMATION: Residues 107-115 of the SCCE protein

<400> SEQUENCE: 90

Gln Thr His Val Asn Asp Leu Met Leu
                5

<210> SEQ ID NO 91
<211> LENGTH: 9
<212> TYPE: PRT
<213> ORGANISM: Homo sapiens
<220> FEATURE:
<221> NAME/KEY: CHAIN
<223> OTHER INFORMATION: Residues 176-184 of the SCCE protein

<400> SEQUENCE: 91

Cys Thr Lys Val Tyr Lys Asp Leu Leu
                5

<210> SEQ ID NO 92
<211> LENGTH: 9
<212> TYPE: PRT
<213> ORGANISM: Homo sapiens
<220> FEATURE:
<221> NAME/KEY: CHAIN
<223> OTHER INFORMATION: Residues 138-146 of the SCCE protein

<400> SEQUENCE: 92

Phe Pro Pro Gly Thr Thr Cys Thr Val
                5

<210> SEQ ID NO 93
<211> LENGTH: 9
<212> TYPE: PRT
<213> ORGANISM: Homo sapiens
<220> FEATURE:
<221> NAME/KEY: CHAIN
<223> OTHER INFORMATION: Residues 70-78 of the SCCE protein

<400> SEQUENCE: 93

His Val Lys Met Asn Glu Tyr Thr Val
                5

<210> SEQ ID NO 94
<211> LENGTH: 9
<212> TYPE: PRT
<213> ORGANISM: Homo sapiens
<220> FEATURE:
<221> NAME/KEY: CHAIN
<223> OTHER INFORMATION: Residues 175-183 of the SCCE protein

<400> SEQUENCE: 94

Asp Cys Thr Lys Val Tyr Lys Asp Leu
                5

<210> SEQ ID NO 95
<211> LENGTH: 9
<212> TYPE: PRT
<213> ORGANISM: Homo sapiens
<220> FEATURE:
```

```
<221> NAME/KEY: CHAIN
<223> OTHER INFORMATION: Residues 119-127 of the SCCE protein

<400> SEQUENCE: 95

Asn Ser Gln Ala Arg Leu Ser Ser Met
                5

<210> SEQ ID NO 96
<211> LENGTH: 9
<212> TYPE: PRT
<213> ORGANISM: Homo sapiens
<220> FEATURE:
<221> NAME/KEY: CHAIN
<223> OTHER INFORMATION: Residues 241-249 of the SCCE protein

<400> SEQUENCE: 96

Phe Thr Lys Trp Ile Asn Asp Thr Met
                5

<210> SEQ ID NO 97
<211> LENGTH: 9
<212> TYPE: PRT
<213> ORGANISM: Homo sapiens
<220> FEATURE:
<221> NAME/KEY: CHAIN
<223> OTHER INFORMATION: Residues 90-98 of the SCCE protein

<400> SEQUENCE: 97

Ala Gln Arg Ile Lys Ala Ser Lys Ser
                5

<210> SEQ ID NO 98
<211> LENGTH: 9
<212> TYPE: PRT
<213> ORGANISM: Homo sapiens
<220> FEATURE:
<221> NAME/KEY: CHAIN
<223> OTHER INFORMATION: Residues 238-246 of the SCCE protein

<400> SEQUENCE: 98

Val Cys Lys Phe Thr Lys Trp Ile Asn
                5

<210> SEQ ID NO 99
<211> LENGTH: 9
<212> TYPE: PRT
<213> ORGANISM: Homo sapiens
<220> FEATURE:
<221> NAME/KEY: CHAIN
<223> OTHER INFORMATION: Residues 91-99 of the SCCE protein

<400> SEQUENCE: 99

Gln Arg Ile Lys Ala Ser Lys Ser Phe
                5

<210> SEQ ID NO 100
<211> LENGTH: 9
<212> TYPE: PRT
<213> ORGANISM: Homo sapiens
<220> FEATURE:
<221> NAME/KEY: CHAIN
<223> OTHER INFORMATION: Residues 62-70 of the SCCE protein

<400> SEQUENCE: 100

Glu Arg Trp Val Leu Thr Ala Ala His
                5

<210> SEQ ID NO 101
```

```
<211> LENGTH: 9
<212> TYPE: PRT
<213> ORGANISM: Homo sapiens
<220> FEATURE:
<221> NAME/KEY: CHAIN
<223> OTHER INFORMATION: Residues 211-219 of the SCCE protein

<400> SEQUENCE: 101

Cys Arg Gly Thr Leu Gln Gly Leu Val
                5

<210> SEQ ID NO 102
<211> LENGTH: 9
<212> TYPE: PRT
<213> ORGANISM: Homo sapiens
<220> FEATURE:
<221> NAME/KEY: CHAIN
<223> OTHER INFORMATION: Residues 135-143 of the SCCE protein

<400> SEQUENCE: 102

Ser Arg Cys Glu Pro Pro Gly Thr Thr
                5

<210> SEQ ID NO 103
<211> LENGTH: 9
<212> TYPE: PRT
<213> ORGANISM: Homo sapiens
<220> FEATURE:
<221> NAME/KEY: CHAIN
<223> OTHER INFORMATION: Residues 37-45 of the SCCE protein

<400> SEQUENCE: 103

Ala Arg Gly Ser His Pro Trp Gln Val
                5

<210> SEQ ID NO 104
<211> LENGTH: 9
<212> TYPE: PRT
<213> ORGANISM: Homo sapiens
<220> FEATURE:
<221> NAME/KEY: CHAIN
<223> OTHER INFORMATION: Residues 227-235 of the SCCE protein

<400> SEQUENCE: 104

Gly Gln Pro Asn Asp Pro Gly Val Tyr
                5

<210> SEQ ID NO 105
<211> LENGTH: 9
<212> TYPE: PRT
<213> ORGANISM: Homo sapiens
<220> FEATURE:
<221> NAME/KEY: CHAIN
<223> OTHER INFORMATION: Residues 236-244 of the SCCE protein

<400> SEQUENCE: 105

Thr Gln Val Cys Lys Phe Thr Lys Trp
                5

<210> SEQ ID NO 106
<211> LENGTH: 9
<212> TYPE: PRT
<213> ORGANISM: Homo sapiens
<220> FEATURE:
<221> NAME/KEY: CHAIN
<223> OTHER INFORMATION: Residues 88-96 of the SCCE protein

<400> SEQUENCE: 106

Arg Arg Ala Gln Arg Ile Lys Ala Ser
```

```
<210> SEQ ID NO 107
<211> LENGTH: 9
<212> TYPE: PRT
<213> ORGANISM: Homo sapiens
<220> FEATURE:
<221> NAME/KEY: CHAIN
<223> OTHER INFORMATION: Residues 87-95 of the SCCE protein

<400> SEQUENCE: 107

Asp Arg Arg Ala Gln Arg Ile Lys Ala
                5

<210> SEQ ID NO 108
<211> LENGTH: 9
<212> TYPE: PRT
<213> ORGANISM: Homo sapiens
<220> FEATURE:
<221> NAME/KEY: CHAIN
<223> OTHER INFORMATION: Residues 233-241 of the SCCE protein

<400> SEQUENCE: 108

Gly Val Tyr Thr Gln Val Cys Lys Phe
                5

<210> SEQ ID NO 109
<211> LENGTH: 9
<212> TYPE: PRT
<213> ORGANISM: Homo sapiens
<220> FEATURE:
<221> NAME/KEY: CHAIN
<223> OTHER INFORMATION: Residues 72-80 of the SCCE protein

<400> SEQUENCE: 109

Lys Met Asn Glu Tyr Thr Val His Leu
                5

<210> SEQ ID NO 110
<211> LENGTH: 9
<212> TYPE: PRT
<213> ORGANISM: Homo sapiens
<220> FEATURE:
<221> NAME/KEY: CHAIN
<223> OTHER INFORMATION: Residues 122-130 of the SCCE protein

<400> SEQUENCE: 110

Ala Arg Leu Ser Ser Met Val Lys Lys
                5

<210> SEQ ID NO 111
<211> LENGTH: 9
<212> TYPE: PRT
<213> ORGANISM: Homo sapiens
<220> FEATURE:
<221> NAME/KEY: CHAIN
<223> OTHER INFORMATION: Residues 120-128 of the SCCE protein

<400> SEQUENCE: 111

Ser Gln Ala Arg Leu Ser Ser Met Val
                5

<210> SEQ ID NO 112
<211> LENGTH: 9
<212> TYPE: PRT
<213> ORGANISM: Homo sapiens
<220> FEATURE:
<221> NAME/KEY: CHAIN
<223> OTHER INFORMATION: Residues 9-17 of the SCCE protein
```

-continued

```
<400> SEQUENCE: 112

Leu Gln Ile Leu Leu Leu Ser Leu Ala
                5

<210> SEQ ID NO 113
<211> LENGTH: 9
<212> TYPE: PRT
<213> ORGANISM: Homo sapiens
<220> FEATURE:
<221> NAME/KEY: CHAIN
<223> OTHER INFORMATION: Residues 215-223 of the SCCE protein

<400> SEQUENCE: 113

Leu Gln Gly Leu Val Ser Trp Gly Thr
                5

<210> SEQ ID NO 114
<211> LENGTH: 9
<212> TYPE: PRT
<213> ORGANISM: Homo sapiens
<220> FEATURE:
<221> NAME/KEY: CHAIN
<223> OTHER INFORMATION: Residues 131-139 of the SCCE protein

<400> SEQUENCE: 114

Val Arg Leu Pro Ser Arg Cys Glu Pro
                5

<210> SEQ ID NO 115
<211> LENGTH: 9
<212> TYPE: PRT
<213> ORGANISM: Homo sapiens
<220> FEATURE:
<221> NAME/KEY: CHAIN
<223> OTHER INFORMATION: Residues 106-114 of the SCCE protein

<400> SEQUENCE: 115

Thr Gln Thr His Val Asn Asp Leu Met
                5

<210> SEQ ID NO 116
<211> LENGTH: 9
<212> TYPE: PRT
<213> ORGANISM: Homo sapiens
<220> FEATURE:
<221> NAME/KEY: CHAIN
<223> OTHER INFORMATION: Residues 2-10 of the SCCE protein

<400> SEQUENCE: 116

Ala Arg Ser Leu Leu Leu Pro Leu Gln
                5

<210> SEQ ID NO 117
<211> LENGTH: 9
<212> TYPE: PRT
<213> ORGANISM: Homo sapiens
<220> FEATURE:
<221> NAME/KEY: CHAIN
<223> OTHER INFORMATION: Residues 99-107 of the SCCE protein

<400> SEQUENCE: 117

Phe Arg His Pro Gly Tyr Ser Thr Gln
                5

<210> SEQ ID NO 118
<211> LENGTH: 9
<212> TYPE: PRT
```

```
<213> ORGANISM: Homo sapiens
<220> FEATURE:
<221> NAME/KEY: CHAIN
<223> OTHER INFORMATION: Residues 137-145 of the SCCE protein

<400> SEQUENCE: 118

Cys Glu Pro Pro Gly Thr Thr Cys Thr
                5

<210> SEQ ID NO 119
<211> LENGTH: 9
<212> TYPE: PRT
<213> ORGANISM: Homo sapiens
<220> FEATURE:
<221> NAME/KEY: CHAIN
<223> OTHER INFORMATION: Residues 61-69 of the SCCE protein

<400> SEQUENCE: 119

Asn Glu Arg Trp Val Leu Thr Ala Ala
                5

<210> SEQ ID NO 120
<211> LENGTH: 9
<212> TYPE: PRT
<213> ORGANISM: Homo sapiens
<220> FEATURE:
<221> NAME/KEY: CHAIN
<223> OTHER INFORMATION: Residues 172-180 of the SCCE protein

<400> SEQUENCE: 120

Ser Pro Gln Asp Cys Thr Lys Val Tyr
                5

<210> SEQ ID NO 121
<211> LENGTH: 9
<212> TYPE: PRT
<213> ORGANISM: Homo sapiens
<220> FEATURE:
<221> NAME/KEY: CHAIN
<223> OTHER INFORMATION: Residues 23-31 of the SCCE protein

<400> SEQUENCE: 121

Glu Glu Ala Gln Gly Asp Lys Ile Ile
                5

<210> SEQ ID NO 122
<211> LENGTH: 9
<212> TYPE: PRT
<213> ORGANISM: Homo sapiens
<220> FEATURE:
<221> NAME/KEY: CHAIN
<223> OTHER INFORMATION: Residues 74-82 of the SCCE protein

<400> SEQUENCE: 122

Asn Glu Tyr Thr Val His Leu Gly Ser
                5

<210> SEQ ID NO 123
<211> LENGTH: 9
<212> TYPE: PRT
<213> ORGANISM: Homo sapiens
<220> FEATURE:
<221> NAME/KEY: CHAIN
<223> OTHER INFORMATION: Residues 22-30 of the SCCE protein

<400> SEQUENCE: 123

Gly Glu Glu Ala Gln Gly Asp Lys Ile
                5
```

```
<210> SEQ ID NO 124
<211> LENGTH: 9
<212> TYPE: PRT
<213> ORGANISM: Homo sapiens
<220> FEATURE:
<221> NAME/KEY: CHAIN
<223> OTHER INFORMATION: Residues 216-224 of the SCCE protein

<400> SEQUENCE: 124

Gln Gly Leu Val Ser Trp Gly Thr Phe
                 5

<210> SEQ ID NO 125
<211> LENGTH: 9
<212> TYPE: PRT
<213> ORGANISM: Homo sapiens
<220> FEATURE:
<221> NAME/KEY: CHAIN
<223> OTHER INFORMATION: Residues 32-40 of the SCCE protein

<400> SEQUENCE: 125

Asp Gly Ala Pro Cys Ala Arg Gly Ser
                 5

<210> SEQ ID NO 126
<211> LENGTH: 9
<212> TYPE: PRT
<213> ORGANISM: Homo sapiens
<220> FEATURE:
<221> NAME/KEY: CHAIN
<223> OTHER INFORMATION: Residues 230-238 of the SCCE protein

<400> SEQUENCE: 126

Asn Asp Pro Gly Val Tyr Thr Gln Val
                 5

<210> SEQ ID NO 127
<211> LENGTH: 9
<212> TYPE: PRT
<213> ORGANISM: Homo sapiens
<220> FEATURE:
<221> NAME/KEY: CHAIN
<223> OTHER INFORMATION: Residues 227-235 of the SCCE protein

<400> SEQUENCE: 127

Gly Gln Pro Asn Asp Pro Gly Val Tyr
                 5

<210> SEQ ID NO 128
<211> LENGTH: 9
<212> TYPE: PRT
<213> ORGANISM: Homo sapiens
<220> FEATURE:
<221> NAME/KEY: CHAIN
<223> OTHER INFORMATION: Residues 111-119 of the SCCE protein

<400> SEQUENCE: 128

Asn Asp Leu Met Leu Val Lys Leu Asn
                 5

<210> SEQ ID NO 129
<211> LENGTH: 9
<212> TYPE: PRT
<213> ORGANISM: Homo sapiens
<220> FEATURE:
<221> NAME/KEY: CHAIN
<223> OTHER INFORMATION: Residues 191-199 of the SCCE protein

<400> SEQUENCE: 129
```

```
Ala Gly Ile Pro Asp Ser Lys Lys Asn
                5

<210> SEQ ID NO 130
<211> LENGTH: 9
<212> TYPE: PRT
<213> ORGANISM: Homo sapiens
<220> FEATURE:
<221> NAME/KEY: CHAIN
<223> OTHER INFORMATION: Residues 91-99 of the SCCE protein

<400> SEQUENCE: 130

Gln Arg Ile Lys Ala Ser Lys Ser Phe
                5

<210> SEQ ID NO 131
<211> LENGTH: 9
<212> TYPE: PRT
<213> ORGANISM: Homo sapiens
<220> FEATURE:
<221> NAME/KEY: CHAIN
<223> OTHER INFORMATION: Residues 236-244 of the SCCE protein

<400> SEQUENCE: 131

Thr Gln Val Cys Lys Phe Thr Lys Trp
                5

<210> SEQ ID NO 132
<211> LENGTH: 9
<212> TYPE: PRT
<213> ORGANISM: Homo sapiens
<220> FEATURE:
<221> NAME/KEY: CHAIN
<223> OTHER INFORMATION: Residues 82-90 of the SCCE protein

<400> SEQUENCE: 132

Ser Asp Thr Leu Gly Asp Arg Arg Ala
                5

<210> SEQ ID NO 133
<211> LENGTH: 9
<212> TYPE: PRT
<213> ORGANISM: Homo sapiens
<220> FEATURE:
<221> NAME/KEY: CHAIN
<223> OTHER INFORMATION: Residues 151-159 of the SCCE protein

<400> SEQUENCE: 133

Thr Thr Thr Ser Pro Asp Val Thr Phe
                5

<210> SEQ ID NO 134
<211> LENGTH: 9
<212> TYPE: PRT
<213> ORGANISM: Homo sapiens
<220> FEATURE:
<221> NAME/KEY: CHAIN
<223> OTHER INFORMATION: Residues 181-189 of the SCCE protein

<400> SEQUENCE: 134

Lys Asp Leu Leu Glu Asn Ser Met Leu
                5

<210> SEQ ID NO 135
<211> LENGTH: 9
<212> TYPE: PRT
<213> ORGANISM: Homo sapiens
<220> FEATURE:
```

```
<221> NAME/KEY: CHAIN
<223> OTHER INFORMATION: Residues 213-221 of the SCCE protein

<400> SEQUENCE: 135

Gly Thr Leu Gln Gly Leu Val Ser Trp
                5

<210> SEQ ID NO 136
<211> LENGTH: 9
<212> TYPE: PRT
<213> ORGANISM: Homo sapiens
<220> FEATURE:
<221> NAME/KEY: CHAIN
<223> OTHER INFORMATION: Residues 141-149 of the SCCE protein

<400> SEQUENCE: 136

Gly Thr Thr Cys Thr Val Ser Gly Trp
                5

<210> SEQ ID NO 137
<211> LENGTH: 30
<212> TYPE: PRT
<213> ORGANISM: Homo sapiens
<220> FEATURE:
<221> NAME/KEY: CHAIN
<223> OTHER INFORMATION: Residues 110-139 of the SCCE protein

<400> SEQUENCE: 137

Val Asn Asp Leu Met Leu Val Lys Leu Asn Ser Gln Ala Arg Leu
                5                  10                  15

Ser Ser Met Val Lys Lys Val Arg Leu Pro Ser Arg Cys Glu Pro
                20                  25                  30

<210> SEQ ID NO 138
<211> LENGTH: 9
<212> TYPE: PRT
<213> ORGANISM: Homo sapiens
<220> FEATURE:
<221> NAME/KEY: CHAIN
<223> OTHER INFORMATION: core binding motifs of HLA DR1, DR4 and DR7

<400> SEQUENCE: 138

Leu Val Lys Leu Asn Ser Gln Ala Arg
                5

<210> SEQ ID NO 139
<211> LENGTH: 9
<212> TYPE: PRT
<213> ORGANISM: Homo sapiens
<220> FEATURE:
<221> NAME/KEY: CHAIN
<223> OTHER INFORMATION: core binding motifs of HLA DR1 and DR4

<400> SEQUENCE: 139

Val Lys Lys Val Arg Leu Pro Ser Arg
                5

<210> SEQ ID NO 140
<211> LENGTH: 9
<212> TYPE: PRT
<213> ORGANISM: Homo sapiens
<220> FEATURE:
<221> NAME/KEY: CHAIN
<223> OTHER INFORMATION: core binding motifs of HLA DR4

<400> SEQUENCE: 140

Leu Met Leu Val Lys Leu Asn Ser Gln
                5
```

```
<210> SEQ ID NO 141
<211> LENGTH: 57
<212> TYPE: PRT
<213> ORGANISM: Homo sapiens
<220> FEATURE:
<221> NAME/KEY: CHAIN
<223> OTHER INFORMATION: amino acids 1 to 57 of TADG-12

<400> SEQUENCE: 141

Val Val Thr Ala Ala His Cys Val Tyr Asp Leu Tyr Leu Pro Lys
                 5                  10                  15

Ser Trp Thr Ile Glu Val Gly Leu Val Ser Leu Leu Asp Gln Pro
                20                  25                  30

Ala Pro Ser His Leu Val Glu Lys Ile Val Tyr His Ser Lys Tyr
                35                  40                  45

Lys Pro Lys Arg Leu Gly Gln Asp Ile Ala Leu Leu
                50                  55

<210> SEQ ID NO 142
<211> LENGTH: 8
<212> TYPE: PRT
<213> ORGANISM: Homo sapiens
<220> FEATURE:
<221> NAME/KEY: CHAIN
<223> OTHER INFORMATION: amino acids 6 to 13 of TADG-12

<400> SEQUENCE: 142

His Cys Val Tyr Asp Leu Tyr Leu
                 5
```